(12) United States Patent
Loghmani et al.

(10) Patent No.: US 11,534,362 B2
(45) Date of Patent: Dec. 27, 2022

(54) QUANTIFICATION OF FORCE DURING SOFT TISSUE MASSAGE FOR RESEARCH AND CLINICAL USE

(71) Applicant: Indiana University Research and Technology Corporation, Indianapolis, IN (US)

(72) Inventors: Mary T. Loghmani, Indianapolis, IN (US); Sohel Anwar, Carmel, IN (US); Ahmed Alotaibi, West Lafayette, IN (US); Keith L. March, Carmel, IN (US); Stanley Chien, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 264 days.

(21) Appl. No.: 15/757,468

(22) PCT Filed: Sep. 16, 2016

(86) PCT No.: PCT/US2016/052164
§ 371 (c)(1),
(2) Date: Mar. 5, 2018

(87) PCT Pub. No.: WO2017/049104
PCT Pub. Date: Mar. 23, 2017

(65) Prior Publication Data
US 2018/0243158 A1 Aug. 30, 2018

Related U.S. Application Data
(60) Provisional application No. 62/219,264, filed on Sep. 16, 2015.

(51) Int. Cl.
*A61H 7/00* (2006.01)
*G16H 20/30* (2018.01)
*G16H 10/60* (2018.01)

(52) U.S. Cl.
CPC ............. *A61H 7/005* (2013.01); *A61H 7/002* (2013.01); *G16H 10/60* (2018.01); *G16H 20/30* (2018.01);
(Continued)

(58) Field of Classification Search
CPC ........ A61H 7/001; A61H 7/003; A61H 7/005; A61H 2201/1207; A61H 2201/1253;
(Continued)

(56) References Cited

U.S. PATENT DOCUMENTS 5,224,469 A * 7/1993 Mocny .................. A61H 39/04
600/587
5,593,381 A 1/1997 Tannenbaum
(Continued)

FOREIGN PATENT DOCUMENTS

NZ 580400 A 3/2012
WO WO2008113139 A1 9/2008
(Continued)

OTHER PUBLICATIONS

International Preliminary Report on Patentability issued by The International Bureau of WIPO, dated Mar. 20, 2018, for International Application No. PCT/US2016/052164; 6 pages.
(Continued)

*Primary Examiner* — Justine R Yu
*Assistant Examiner* — Alexander Morales
(74) *Attorney, Agent, or Firm* — Faegre Drinker Biddle & Reath LLP

(57) ABSTRACT

A manually-operated quantification soft tissue mobilization (QSTM) device includes a pressure applicator and a sensor
(Continued)

member. The pressure applicator is configured to enable a user to dynamically apply a stroking mechanical force as the pressure applicator is moved over an area treatment areas of a patient's soft tissue. The sensor member including an accelerometer and a gyrometer is configured to determine various parameters of the dynamically applied stroking mechanical force in three dimensions as the pressure applicator is moved over the treatment areas of the patient's soft tissue. These parameters include a force magnitude in three dimensions, an angle in multiple axes, a stroke position, a stroke frequency, a sensed vibration magnitude at dominant spectral frequencies, and/or a rate of the stroking mechanical force dynamically applied to the soft tissue.

48 Claims, 33 Drawing Sheets

(52) U.S. Cl.
CPC .............. *A61H 7/001* (2013.01); *A61H 7/003* (2013.01); *A61H 2201/1207* (2013.01); *A61H 2201/1253* (2013.01); *A61H 2201/1635* (2013.01); *A61H 2201/1664* (2013.01); *A61H 2201/5012* (2013.01); *A61H 2201/5043* (2013.01); *A61H 2201/5061* (2013.01); *A61H 2201/5064* (2013.01); *A61H 2201/5069* (2013.01); *A61H 2201/5071* (2013.01); *A61H 2201/5084* (2013.01); *A61H 2201/5097* (2013.01)

(58) Field of Classification Search
CPC .... A61H 2201/1635; A61H 2201/1664; A61H 2201/5012; A61H 2201/5043; A61H 2201/5061; A61H 2201/5064; A61H 2201/5069; A61H 2201/5071; A61H 2201/5084; A61H 2201/5097; G16H 10/60; G16H 20/30
USPC .......................................................... 601/41
See application file for complete search history.

(56) References Cited

U.S. PATENT DOCUMENTS

| | | | | |
|---|---|---|---|---|
| 5,791,350 | A * | 8/1998 | Morton | A61B 5/224 600/587 |
| 5,817,037 | A * | 10/1998 | Zurbay | A61H 7/003 601/135 |
| 6,063,044 | A * | 5/2000 | Leonard | A61B 5/0053 600/587 |
| 6,267,738 | B1 * | 7/2001 | Louis | A61H 1/008 601/118 |
| 6,871,413 | B1 * | 3/2005 | Arms | A61B 5/1071 33/1 N |
| 8,491,509 | B2 | 7/2013 | Trandafir | |
| 8,574,179 | B2 | 11/2013 | Kline | |
| 8,656,759 | B2 * | 2/2014 | Hughes | G01N 3/42 73/78 |
| 9,326,703 | B2 * | 5/2016 | Leathers | A61B 5/103 |
| 9,655,813 | B2 * | 5/2017 | Leckenby | A61N 1/36034 607/59 |
| 2002/0055694 | A1 * | 5/2002 | Halperin | A61B 5/742 601/41 |
| 2006/0270956 | A1 * | 11/2006 | Wong | A61H 39/04 601/108 |
| 2007/0270727 | A1 | 11/2007 | Khorassani | |
| 2008/0171311 | A1 * | 7/2008 | Centen | G16H 20/30 434/265 |
| 2010/0191160 | A1 * | 7/2010 | Avramovich | A61H 15/02 601/94 |
| 2010/0286569 | A1 * | 11/2010 | Nagano | A61H 1/008 601/84 |
| 2011/0054367 | A1 * | 3/2011 | Schulz | A61H 23/0218 601/46 |
| 2012/0330194 | A1 * | 12/2012 | Britva | A61H 7/005 601/2 |
| 2013/0085551 | A1 * | 4/2013 | Bachinski | A61N 1/36034 607/59 |
| 2014/0031729 | A1 * | 1/2014 | Belalcazar | A61M 16/0677 601/41 |
| 2014/0031866 | A1 * | 1/2014 | Fuhr | A61H 1/008 606/239 |
| 2014/0135666 | A1 * | 5/2014 | Butler | A61H 31/007 601/41 |
| 2014/0163437 | A1 * | 6/2014 | Mack | A61H 19/30 601/46 |
| 2014/0213942 | A1 * | 7/2014 | Hanson | A61H 31/005 601/43 |
| 2014/0243611 | A1 * | 8/2014 | Ishikawa | A61B 5/0042 600/301 |
| 2015/0005679 | A1 * | 1/2015 | Becse | A61B 5/0533 601/15 |
| 2015/0182415 | A1 * | 7/2015 | Olkowski | A61F 9/00772 601/93 |
| 2015/0272820 | A1 * | 10/2015 | Holifield | A61M 16/0677 601/41 |
| 2015/0305974 | A1 * | 10/2015 | Ehrenreich | A61H 23/0236 601/46 |
| 2016/0089296 | A1 * | 3/2016 | Swart | A61B 17/22004 601/108 |
| 2016/0136042 | A1 * | 5/2016 | Nilsson | A61H 1/008 600/587 |

FOREIGN PATENT DOCUMENTS

| | | | |
|---|---|---|---|
| WO | WO2013006264 A2 | 1/2013 | |
| WO | WO-2015038005 A3 * | 5/2015 | ............. A61H 23/04 |
| WO | 2017049104 | 3/2017 | |

OTHER PUBLICATIONS

International Search Report and Written Opinion issued by the ISA/US, Commissioner for Patents, dated Dec. 7, 2016, for International Application No. PCT/US2016/052164; 7 pages.

Kumar S., Beaton K., Hughes T., The Effectiveness of massage therapy for the treatment of nonspecific low back pain: a systematic review of systematic reviews. International J. General Med. 2013; 6: 733-774.

Massage therapy attenuates inflammatory signaling after exercise-induced muscle damage. Science Transl. Med. 2013; 4:1-8.

Best TM, Crawford SK, Haas C, Charles L, Zhao Y. Transverse forces in skeletal muscle with massage-like loading in a rabbit model. MBC Complementary and Iternative Medicine 2014; 14: 393.

Davidson CJ, Ganion LR, Gehlsen GM, Verhoestra B, Roepke JE, Sevier,TL. Rat tendon morphologic and functional changes resulting from soft tissue mobilization. Med Sci Sports Exerc. 1997; 29: 313-319.

Gehlsen GM, Ganion LR, Helfst R. Fibroblast responses to variation in soft tissue mobilization pressure. Med Sci Sports Exerc. 1999; 31: 531-535.

Loghmani MT, Warden SJ, Instrument-Assisted Soft Tissue Mobilization Accelerates Knee Ligament Healing, JOSPT. 2009; 39: 506-14.

Loghmani MT, Warden SJ, Instrument-assisted cross fiber massage increases tissue perfusion and alters micro-vascular morphology in the vicinity of healing knee ligaments. MBC Complementary and Alternative Medicine, 2013; 13: 1-9.

Looney B, Srokose T, et al. Graston Instrument Soft Tissue Mobilization and Home Stretching for the Management of Plantar Heel Pain: A Case Series. J Manipulative Physiol Ther. 2011; 34: 138-142.

(56) References Cited

OTHER PUBLICATIONS

Bayliss AJ, Kiene F, Gundeck E, Loghmani MT, Treatment of a patient with post-natal chronic calf pain utilizing instrument-assisted soft tissue mobilization: a case study. JMMT, 2011; 19-: 1-8.

McCrea EC, George SZ, Outcomes following arugumented soft tissue mobilization for patients with knee pain: A case series, Orthopedic Physical Therapy Practice, 2010; 22: 69-74.

Burke J, Buchberger DJ, Carey-Loghmani MT, Dougherty PE, Greco DS, Dishman JD, A pilot study comparing two manual therapy interventions for carpal tunnel syndrome, JMMT, 2007; 30: 50-61.

Wang Q, Zeng H, Best TM, Haas C, Heffner NT, Agarwal S, Zhao Y., A mechatronic system for quantitative application and assessment of massage-like actions in small animals, Annals of biomedical engineering 2014; 42(1) 36-49.

Haas C, Butterfield TA, Zhao Y, Zhang X, Jarjoura D, Best TM, Dose-dependency of massage-like compressive loading on recovery of active muscle properties following eccentric exercise: rabbit study with clinical relevance, BR J Sports Med, 2013; 47: 83-88.

Haas C, Butterfield TA, Abshire S, Zhang X, Jarjoura D, Best TM, Massage timing affects postexercise muscle recovery and inflammation in a rabbit model, Med Sci Sport Exer. 2013; 1105-1112.

Haas C, Best TM, Wang Q, Butterfield TA, Zhao Y, In vivo passive mechanical properties of skeletal muscle improve with massage-like loading following eccentric exercise, J Biomechanics, 2012; 45: 2630-2636.

Butterfield TA, Zhao Y, Agarwal S, Haq F, Best TM, Cyclic compressive lading facilitates recovery after eccentric exercise, Med Sci Sports Excer. 2008; 1289-1296.

Zeng H, Butterfield TA, Agarwal S, Haq F, Best TM, Zhao Y, An engineering approach for quantitative analysis of the lengthwise strokes in massage therapies, J Medical Devices, 2008; 2:1-8.

Vardiman JP, Siedlik J, Herda T, Hawkins W, Cooper M Graham ZA, Eckert J, Gallagher P, Instrument-assisted soft tissue mobilization: effects on the properties of human plantar flexors, Int J Sports Med, Oct. 2014, DOI: 10.1055/s-0034-1384543.

Lee H, Wu S, You J, Quantitative application of transverse friction massage and its neurological effects on flexor carpi radialis. Manual Therapy, 2009; 14: 501-507.

Huang C, BHolfeld J, Schaden W, Orgill D, Ogawa R, Mechanotherapy: revisiting physical therapy and recruiting mechanobiology for a new era in medicine, Cell, 2013; 19(9): 555-564.

Best TM, Gharibeh B, Huard J, Stem cells, angiogenesis and muscle healing: a potential role in massage therapies? BMJ, 2013; 47: 556-560.

Langevin HL, Stevens-Tuttle D, Fox Jr. Badger GJ, Bouffard NA, et al., Ultrasound evidence of altered lumbar connective tissue structure in human subjects with chronic low back pain, MBC Musculoskeletal Disorders, 2009; 9: 1-9.

Weerapong P, Hume PA, Kilt GS, The mechanisms of massage and effects on performance, muscle recovery and injury prevention. Sports Med, 2005; 35(3): 235-256.

Justin D. Crane, et al., Exercise-Induced Muscle Damage Massage Therapy Attenuates Inflammatory Signaling After Improve LB soft tissue quality Sci Transl Med, 2012; 4:1-8.

\* cited by examiner

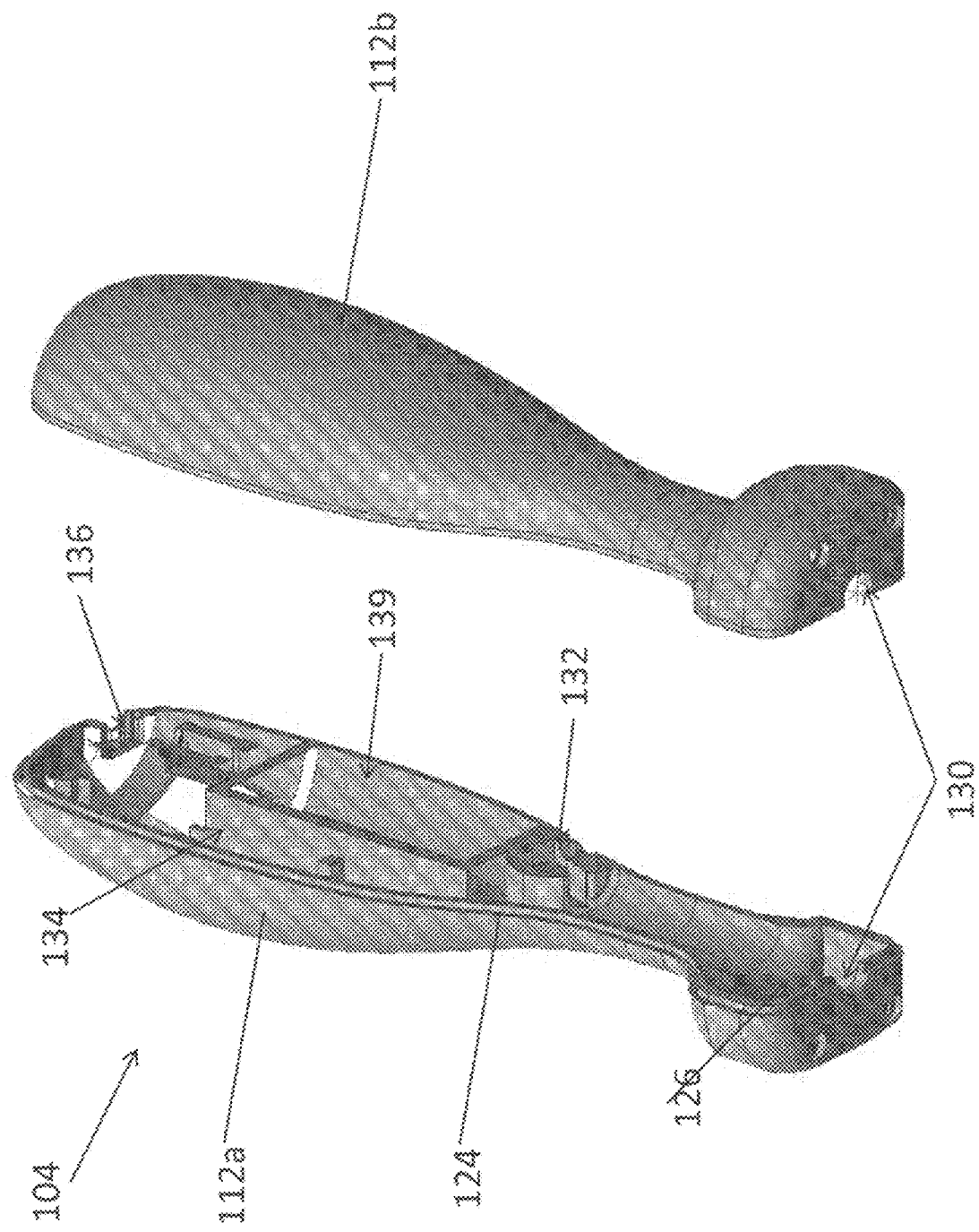

QUANTIFICATION OF FORCE DURING SOFT TISSUE MASSAGE FOR RESEARCH AND CLINICAL USE

CROSS-REFERENCE TO RELATED APPLICATIONS

The present application is a national stage application under 35 U.S.C. § 371 of International Patent Application No. PCT/US2016/052164, filed Sep. 16, 2016, which in turn claims priority from U.S. Provisional Application Ser. No. 62/219,264, filed Sep. 16, 2015, and entitled "QUANTIFICATION OF FORCE DURING SOFT TISSUE MASSAGE FOR RESEARCH AND CLINICAL USE", the complete disclosures of which are expressly incorporated herein by reference.

FIELD OF THE DISCLOSURE

The present disclosure relates to quantifying a force applied to soft tissue and, more particularly, to a device and method for quantifying at least a force magnitude and angle in one or more dimensions, duration, stroke length, and/or rate/frequency of force and its motion trajectory applied to soft tissue through a manual (hand-held) instrument-assisted soft tissue mobilization in real time. The device configured for such quantification may be referred to as a quantification soft tissue mobilization ("QSTM") device.

BACKGROUND OF THE DISCLOSURE

Massage-based therapies, such as soft tissue mobilization or manipulation ("STM"), may be used for improving soft tissue quality in patients with acute injuries, chronic injuries, and/or diseases (e.g., knee pain, plantar fasciitis, carpal tunnel syndrome). For example, massage-base therapies may improve the structure, function, and/or the blood flow of the cells at a specific portion of soft tissue.

One such massage-based therapy is instrument-assisted soft tissue mobilization ("IASTM"), in which a physical therapist, occupational therapist, chiropractor, doctor, athletic trainer, and/or any other professional trained in massage applies pressure to the soft tissue (e.g., muscle, tendon, ligament, and/or fascia) of a patient with a rigid device. Cells within the soft tissue are load sensitive and massage-based therapies, such as QSTM and IASTM, are forms of mechanotherapy which provide direct mechanical stimuli to the cells to promote endogenous tissue healing, repair, and regeneration.

However, IASTM therapies are not uniformly applied to specific injuries or parts of the patient's body because the pressure applied to the soft tissue is dependent upon the person applying the pressure. This makes IASTM and other massage-based therapies difficult to replicate, compare, determine the treatment effect, or monitor progress such that the patient may not receive consistent, progressive, or optimized care for a particular injury or disease. "Patient" may refer to both humans and animals who may be under clinical care and/or research subjects enrolled in a research protocol. It is useful to minimize differences in the application of STM by different therapists, doctors, clinicians, or others and also is useful to minimize differences in the application of STM by the same therapist, doctor, or clinician between different therapy sessions. As such, there is a need for a device and/or method for quantifying the pressure applied to soft tissue through massage-based therapies.

SUMMARY OF THE DISCLOSURE

In one embodiment, a manual (i.e., handheld) quantification soft tissue mobilization (QSTM) device may be mechanical or electronic, portable, and easily maneuverable. The QSTM device includes a pressure applicator and a sensor member configured to determine at least one of a magnitude in three dimensions, an angle in multiple axes, a stroke frequency, and a rate of a force dynamically applied over an area of soft tissue by the pressure applicator.

In another embodiment, a method of quantifying a force dynamically applied to soft tissue includes sensing at least one of a magnitude in three dimensions, an angle in multiple axes, a duration, a stroke frequency, and a rate of the force dynamically applied over an area of the soft tissue. The method also includes transmitting an output of at least one of the magnitude, angle, duration, stroke frequency, and rate of the force. Additionally, the method includes visually indicating the output of at least one of the magnitude, angle, duration, stroke frequency, and rate of the force.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The foregoing aspects and many of the intended advantages of this invention will become more readily appreciated as the same becomes better understood by reference to the following detailed description when taken in conjunction with the accompanying drawings.

FIG. 7A is a schematic view of an alternative embodiment pressure applicator of the present disclosure;

FIG. 15 is an exploded view of a handle portion of the alternative soft tissue mobilization system of FIG. 13;

Figure 1:
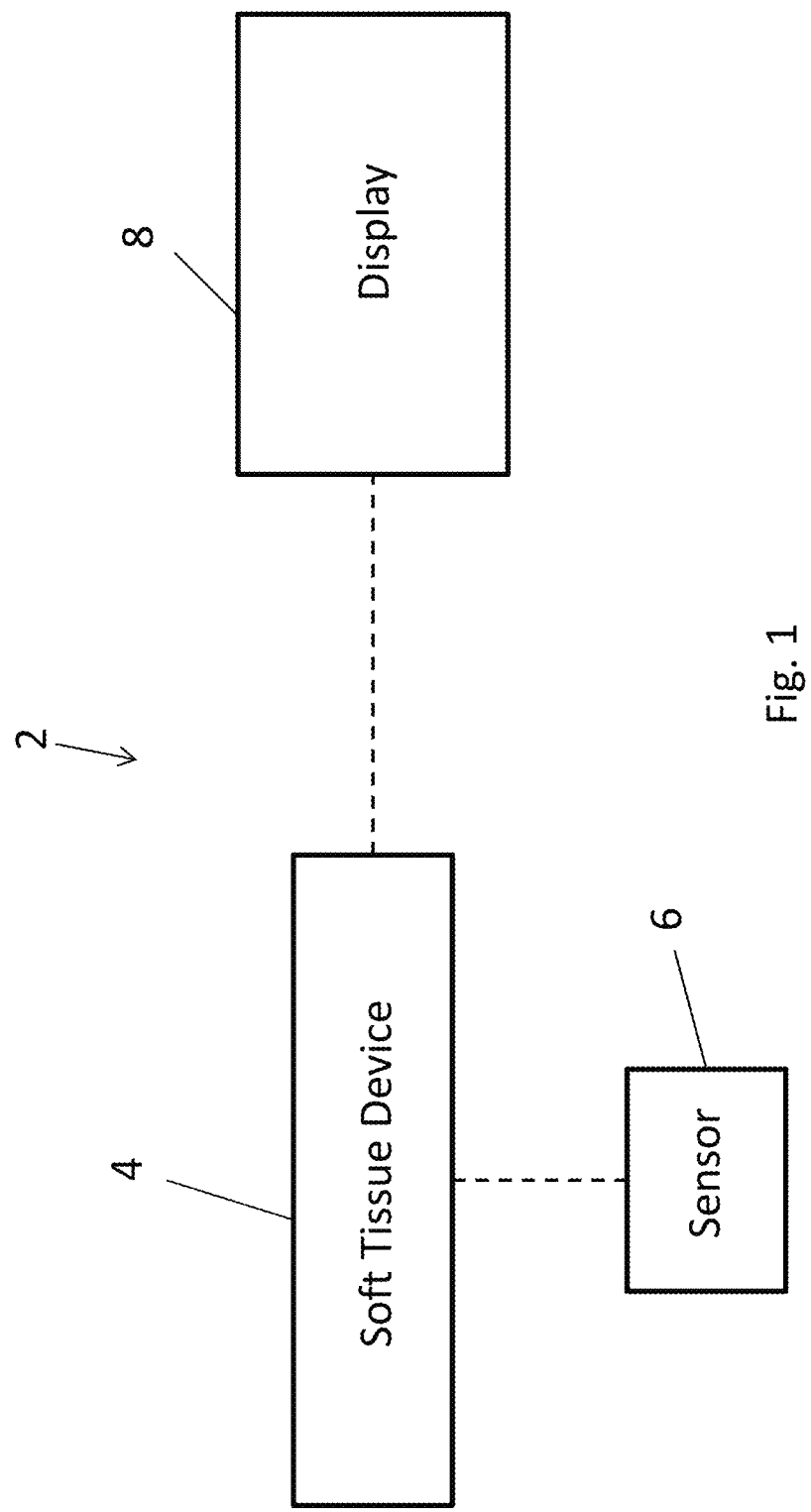
FIG. 1 is a schematic view of a soft tissue mobilization system of the present disclosure.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein illustrate embodiments of the invention, and such exemplifications are not to be construed as limiting the scope of the invention in any manner.

DETAILED DESCRIPTION OF THE DRAWINGS

For the purposes of promoting an understanding of the principals of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrative devices and described methods and further applications of the principles of the invention which would normally occur to one skilled in the art to which the invention relates.

Figure 33:
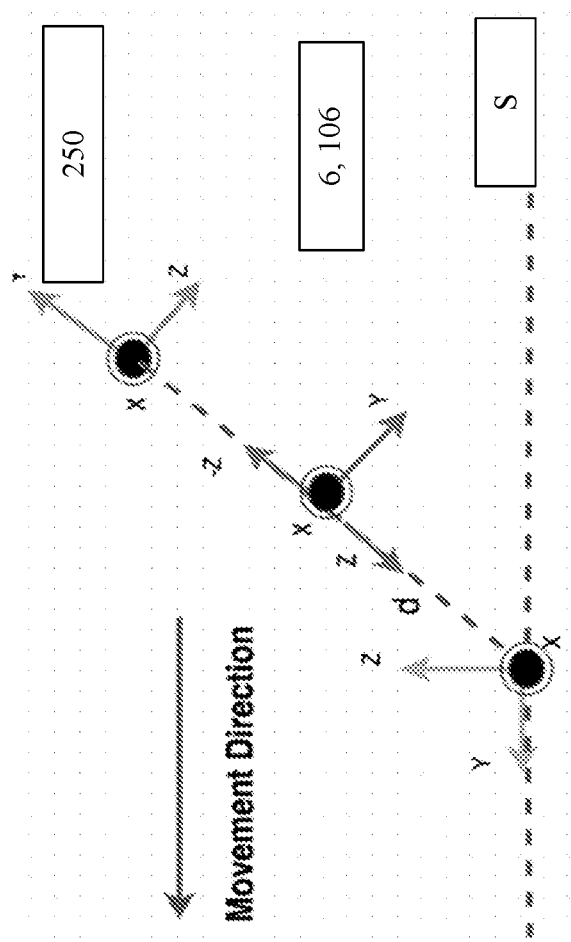
FIG. 33 is a diagram view of different coordinate systems for different components of the soft tissue mobilization system.

Referring to FIG. 1, a soft tissue mobilization system 2 includes a soft tissue device 4 configured for QSTM or IASTM and which is electronically coupled to at least one sensor member 6 and a user interface, illustratively a visual display 8. Soft tissue mobilization system 2 is configured to quantify the pressure applied to the soft tissue of a patient during a massage-based therapy, such as QSTM, in real time. "Patient" referred to herein may be any human or animal under clinical care and/or any research subject enrolled in research testing, a protocol, a research procedure, etc. More particularly, "real time" refers to immediate quantification and output of data during QSTM such that no delay or a minimal delay (i.e., less than 2 seconds) occurs between measuring the force or pressure applied to the patient's soft tissue S (see FIG. 33) and providing the output to visual display 8. For example, soft tissue mobilization system 2 is configured to measure and output the magnitude, rate, duration, and/or angle of the force applied to soft tissue device 4 by a doctor, therapist, clinician, or other professional to quantify the force applied to the soft tissue of the patient. In one embodiment, sensor member 6 is configured to measure up to 155 N (35 lbs.) of force applied to soft tissue device 4.

Illustrative soft tissue mobilization system 2 wirelessly transmits the pressure data between soft tissue device 4, sensor member 6 (e.g., a three-dimensional load cell), and/or visual display 8. For example, soft tissue mobilization system 2 may utilize Bluetooth technology (e.g., a Bluetooth transmitter), Zigbee, or other wireless protocols ("Wifi") to wirelessly transmit sensor information. In this way, soft tissue mobilization system 2 is a self-contained and, therefore, portable system for administering and quantifying pressure to the soft tissue of a patient. Alternatively, soft tissue mobilization system 2 or components thereof may be added to existing QSTM systems to also measure real-time force quantification data.

Additionally, because sensor member 6 wirelessly transmits the force quantifications, visual display 8 can be positioned at any convenient location that can be viewed by the doctor, therapist, clinician, or professional administering the soft tissue massage to the patient. Without any wires connecting QSTM soft tissue device 4 to visual display 8, the doctor, therapist, clinician, or professional administering the soft tissue massage is free to move about the room and the patient, all the while being able to view the real-time force quantifications displayed on visual display 8. In one embodiment, visual display 8 may be any LED or LCD monitor, display, screen, or other device configured to display the force quantification data from soft tissue device 4 in real time.

Alternatively, visual display 8 may be an audio device configured to output a sound to the doctor, clinician, therapist, nurse, or other professional administering QSTM. Additionally, visual display 8 may include both an audio output and a visual output.

A computing device, including at least memory and a processor or microprocessor configured to receive machine-readable instructions or software (not shown), is operably coupled to visual display. In one embodiment, visual display 8 and the computing device collectively comprise a computer, such as a laptop or desktop computer, or a tablet device. For example, the computing device (not shown) may be a PC, Android, or OSX based device. As such, sensor member 6 and/or soft tissue device 4 is configured to transmit sensed data to the computing device and the processor is configured to convert the sensed data to various units which may be best understood by the user. For example, the sensed data may be translated or otherwise converted into a coordinate system for indicating longitudinal motion along the y-axis, lateral motion along the x-axis, and vertical motion along the z-axis normal to the soft tissue of the patient.

Figure 2:
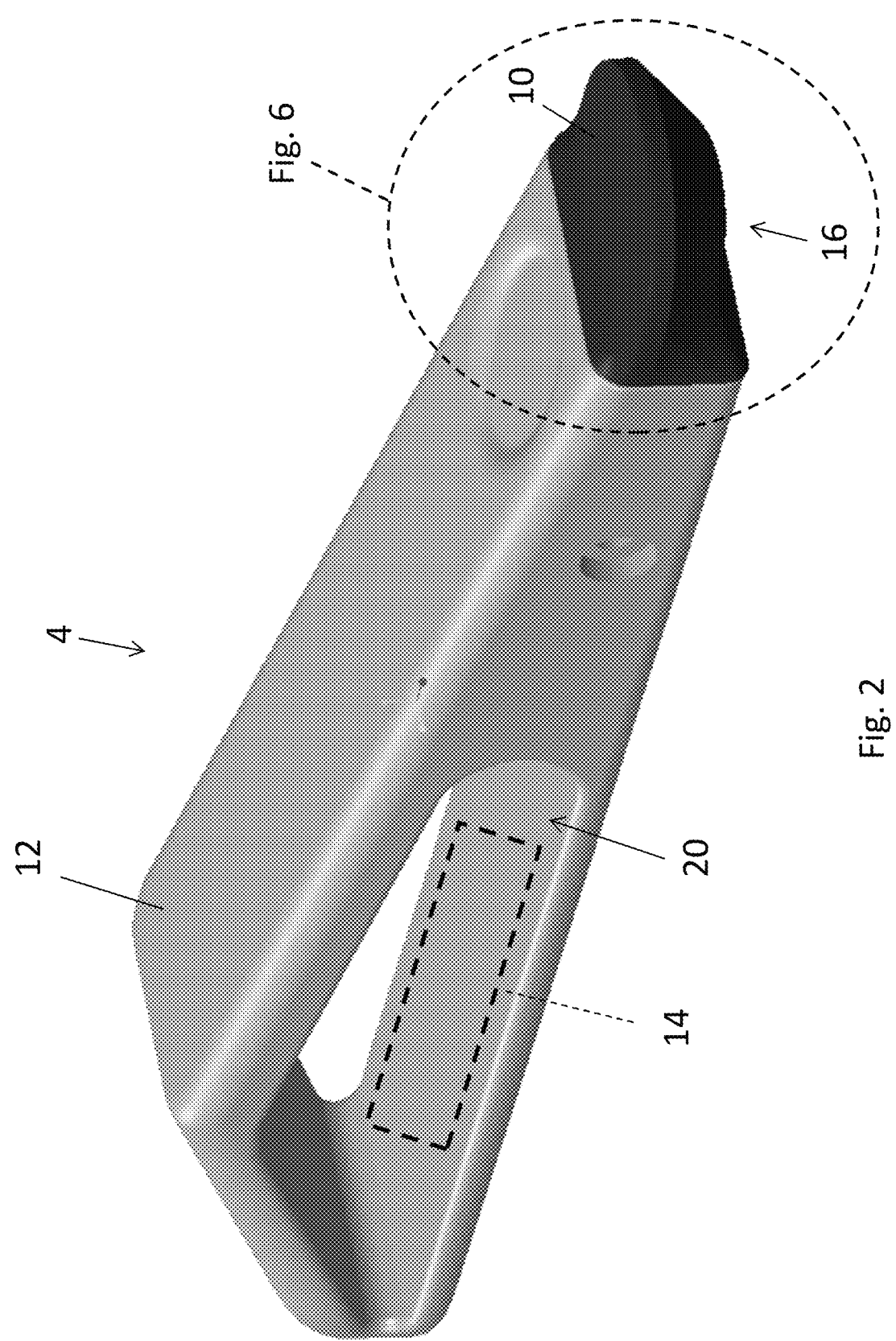
FIG. 2 is a perspective view of a manual soft tissue device of the soft tissue mobilization system of FIG. 1.
Figure 3:
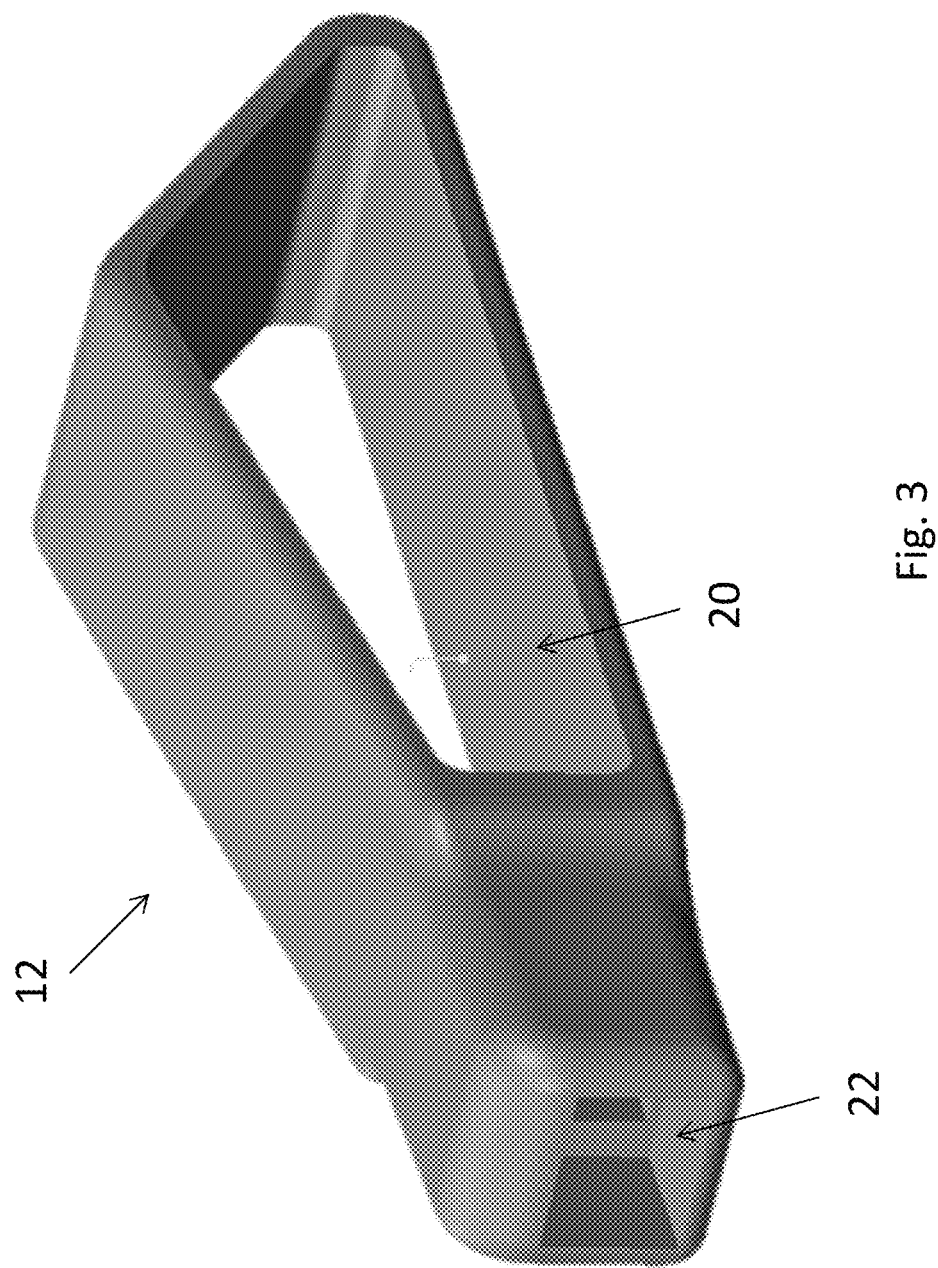
FIG. 3 is a perspective view of a handle of the soft tissue device of FIG. 2.
Figure 4:
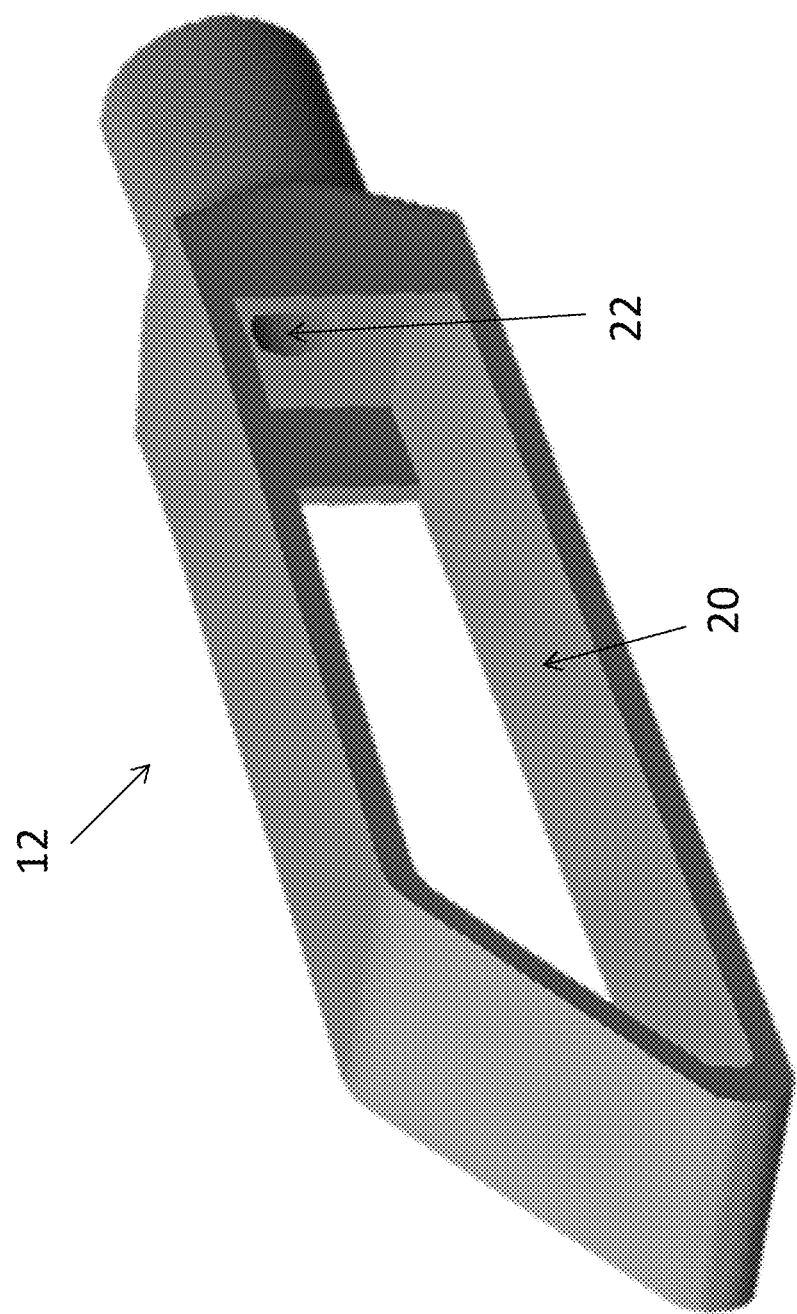
FIG. 4 is a further perspective view of the handle of FIG. 3.

Referring to FIGS. 2-5, soft tissue device 4 is a portable, maneuverable, electronic, and manual (i.e., handheld) examination and treatment device which includes a pressure applicator 10, a handle 12, and an electronic assembly 14. As shown in FIGS. 3 and 4, in one embodiment, handle 12 is a rigid member which extends from pressure applicator 10. Illustrative handle 12 has a polygonal shape which generally defines a triangle, however, handle 12 may have any configuration. Handle 12 may be comprised of a polymeric material and may be formed through molding processes (e.g., casting, compression molding), stereolithography, fused deposition modeling, or three-dimensional printing. For example, handle 12 may be comprised of thermoplastic and/or fibrous composite material. Alternatively, handle 12 may be comprised of any other material, for example a metallic material. Handle 12 is configured to be grasped by a doctor, therapist, clinician, or other professional to manually apply pressure to the soft tissue of a patient.

In one embodiment, handle 12 supports or houses electronic assembly 14. In one example, handle 12 includes an opening 20 which is configured to support electronic assembly 14. Electronic assembly 14 is electronically coupled to sensor member 6 and visual display 8 (FIG. 1), as disclosed further herein, and may utilize Bluetooth or other wireless technology (e.g., a Bluetooth transmitter) to wirelessly transmit information between sensor member 6, soft tissue device 4, and/or visual display 8 (FIG. 1).

Handle 12 also includes a channel 22 which is configured to receive pressure applicator 10. Illustrative channel 22 defines a rectangle in cross-section but may define any other shape in cross-section. Channel 22 opens to opening 20 such that pressure applicator 10 may be electronically coupled to electronic assembly 14, either wirelessly or through a wired connection.

Figure 5:
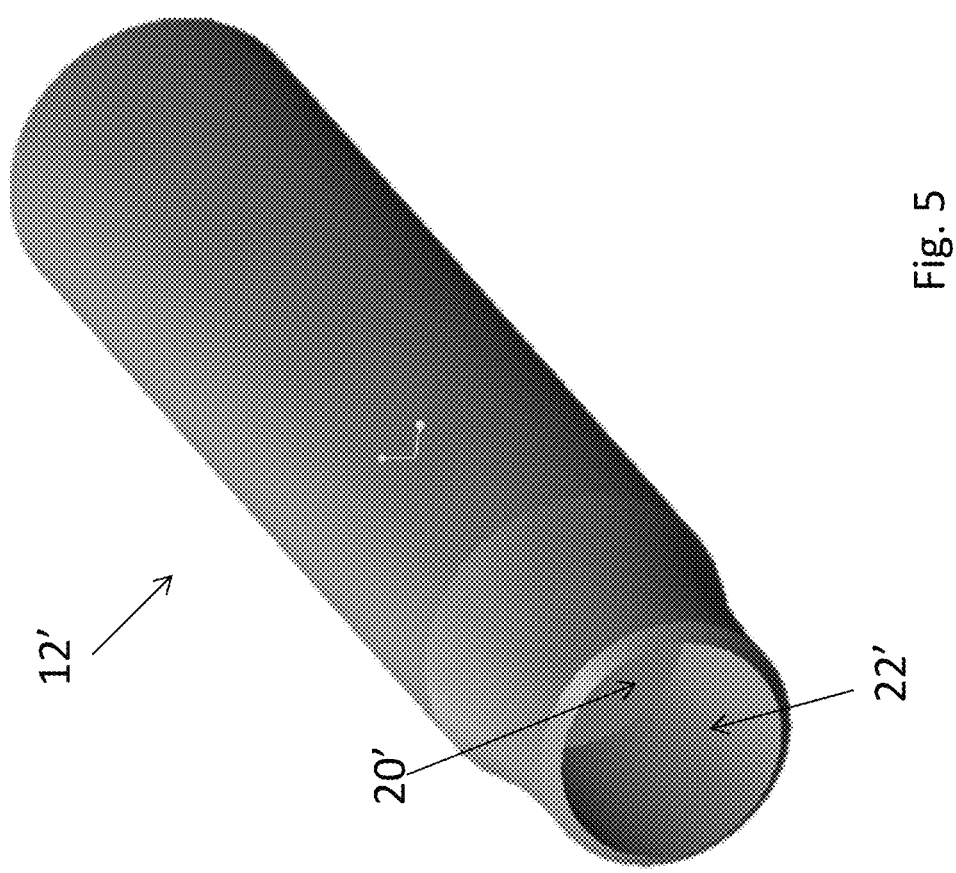
FIG. 5 is a perspective view of an alternative embodiment handle of the soft tissue device of FIG. 2.

Referring to FIG. 5, an alternative embodiment handle 12' is disclosed. Handle 12' extends longitudinally to define a cylindrical shape with a circular cross-section. Handle 12' includes a channel 22' for receiving pressure applicator 10 (FIG. 2). Channel 22' opens to an opening 20' within handle 12' which may support or house electronic assembly 14 (FIG. 2). Similar to handle 12, handle 12' may be comprised of a polymeric material and is formed through a molding, stereolithography, fused deposition modeling, or three-dimensional printing process.

Figure 6:
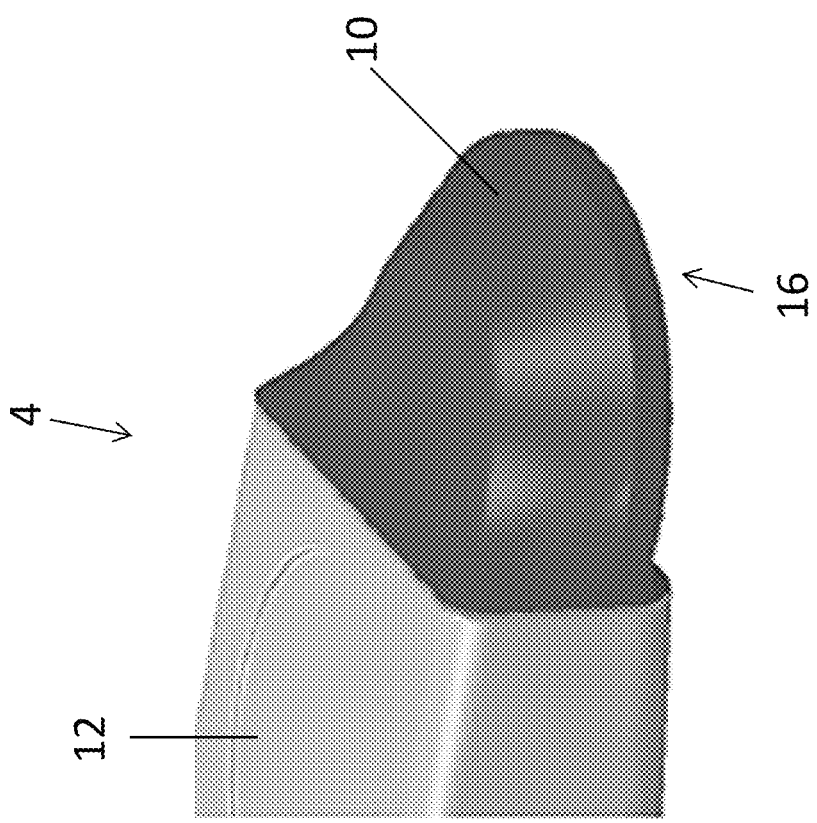
FIG. 6 is a detailed view of a pressure applicator of the soft tissue device of FIG. 2.
Figure 7:
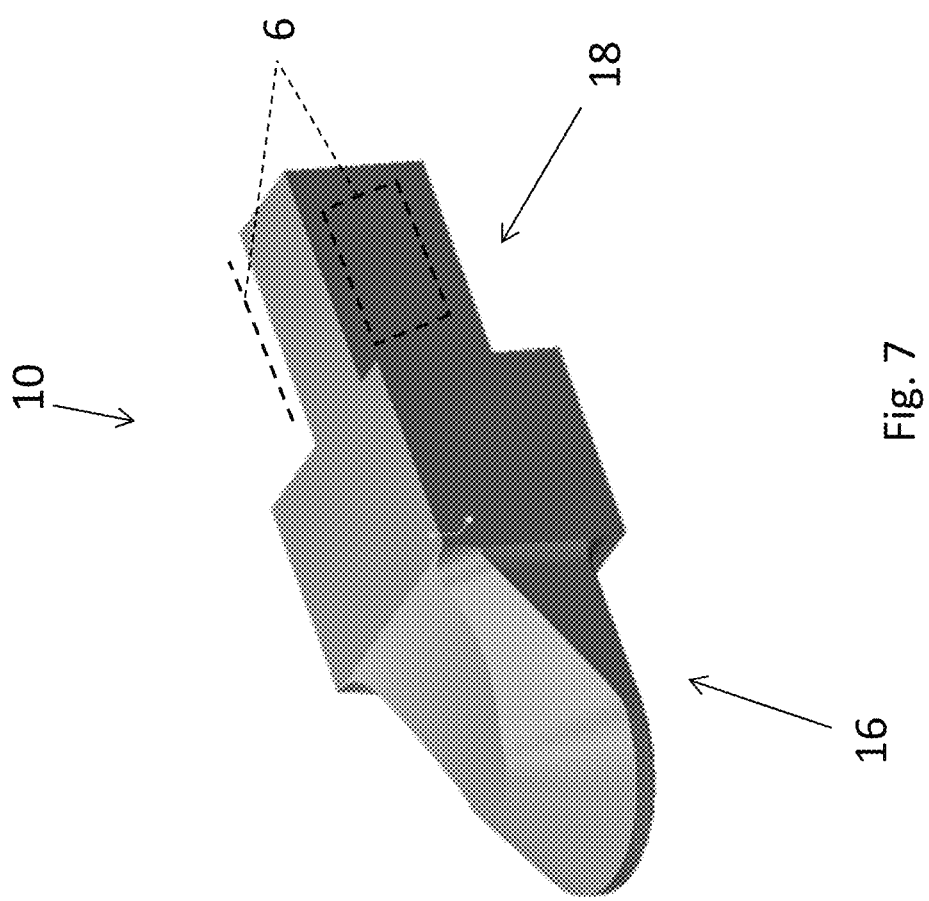
FIG. 7 is a perspective view of the pressure applicator of FIG. 6.

As shown in FIGS. 2, 6, and 7, pressure applicator 10 of soft tissue device 4 includes a first end 16 and a second end 18. First end 16 is configured to contact the soft tissue of the patient while second end 18 is spaced apart from the soft tissue. More particularly, first end 16 defines a flat or plate-like surface configured to contact the soft tissue or soft tissue of the patient and transfer pressure to the soft tissue when the doctor, therapist, or other clinician or professional applies a force to soft tissue device 4, as disclosed further herein.

In one embodiment, second end 18 of pressure applicator 10 is received within channel 22 of handle 12 and may have a shape complementary to that of channel 22 of handle 12. Alternatively, second end 18 may be integrally formed with handle 12. Pressure applicator 10 is comprised of a metallic and/or polymeric material. For example, pressure applicator 10 may be comprised of stainless steel or, alternatively, a carbon-based material and/or a polymeric resin with a hardness similar to that of stainless steel. By comprising pressure applicator 10 of stainless steel, a carbon-based material, and/or a polymeric resin, the doctor, therapist, clinician, or other professional manually applying force to soft tissue device 4 is able to receive "feedback" in the form or vibrations from the soft tissue transmitted back to the doctor, therapist, clinician, or other professional through pressure applicator 10.

As shown in FIG. 7, second end 18 of pressure applicator 10 includes sensor member 6. In one embodiment, sensor member 6 may be coupled to or retained on second end 18 of pressure applicator 10. Alternatively, sensor member 6 may be integrally formed with second end 18 of pressure applicator 10. In a further embodiment, sensor member 6 may be spaced apart from pressure applicator 10 but electronically coupled thereto to wirelessly transmit information between pressure applicator 10 and sensor member 6. In yet another embodiment, sensor member 6 may be positioned on or within handle 12 rather than pressure applicator 10. When second end 18 of pressure applicator 10 is received within channel 22 of handle 12, sensor member 6 is positioned at the interface therebetween. However, a tolerance is provided at the interface between second end 18 of pressure applicator 10 and handle 12 so as to not pre-load sensor member 6 with tension or compression from the coupling between pressure applicator 10 and handle 12 prior to measuring the force applied to soft tissue device 4. As such, sensor member 6 accurately measures only the force applied to the soft tissue by soft tissue device 4 without any inaccuracies from the coupling of pressure applicator 10 and handle 12.

Because sensor member 6 is spaced apart from first end 16 of pressure applicator 10, sensor member 6 does not contact the soft tissue of the patient. As such, sensor member 6 is protected from friction and/or body oils from the soft tissue which increases the operating life of sensor member 6. Additionally, because the soft tissue may have varying contours and is not a flat surface, the output from sensor member 6 may not be an accurate measure of the force applied to soft tissue device 4 if sensor 6 was directly applied to the soft tissue. Therefore, by spacing sensor member 6 apart from the soft tissue and first end 16 of pressure applicator 10, the output from sensor member 6 may more accurately quantify the force applied by the doctor, therapist, clinician, or other professional through soft tissue device 4.

Figure 11:
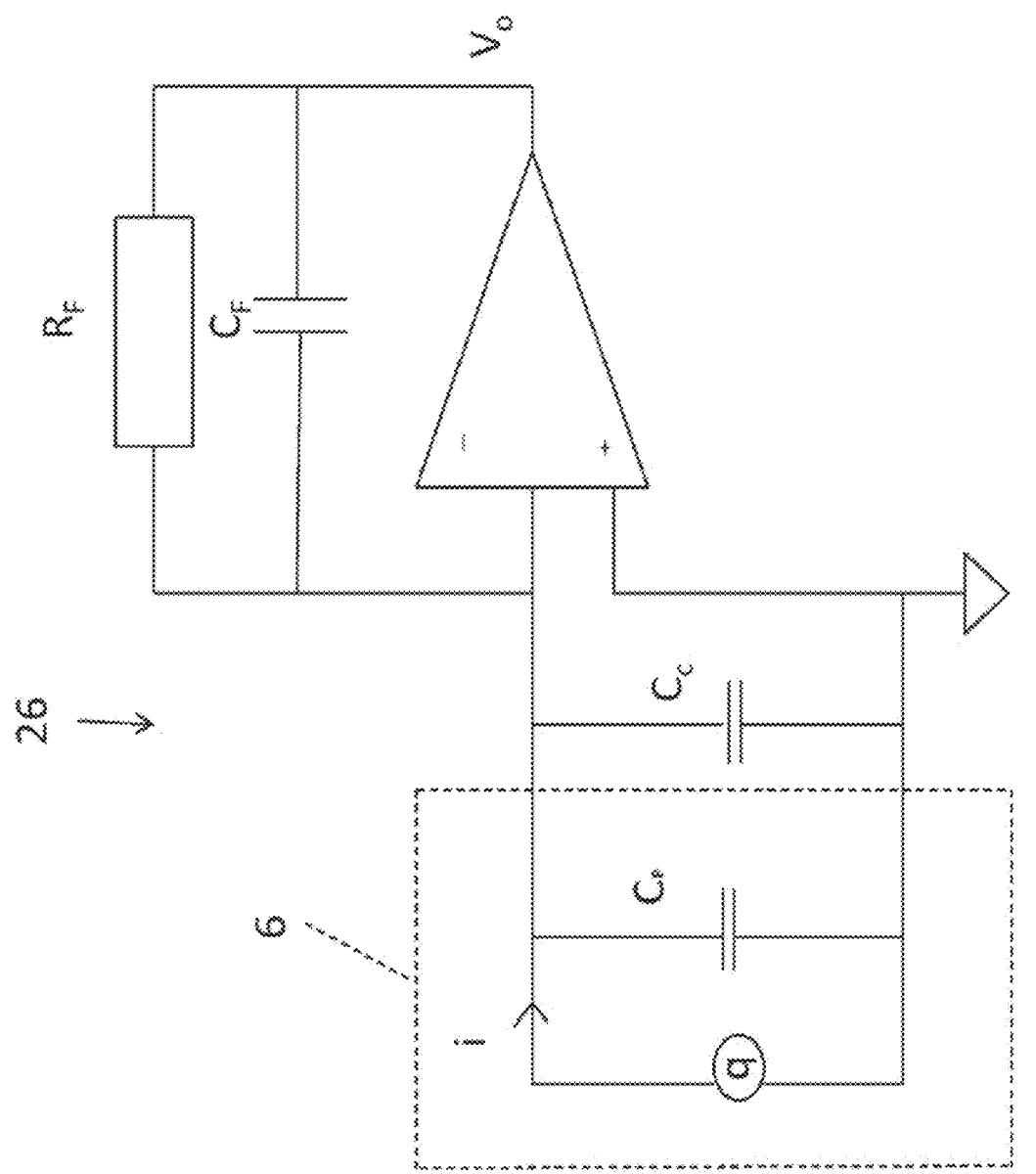
FIG. 11 is a circuit diagram for amplifying an output from the soft tissue device.

In one embodiment, sensor member 6 is a piezoresistive-type or a strain gauge-type sensor. If sensor member 6 is a piezoresistive-type sensor, a conditioning circuit or charge amplification circuit 26 may be provided to facilitate the output from sensor member 6, as shown in FIG. 11.

Sensor member 6 is configured to quantify the force applied to the soft tissue by soft tissue device 4. More particularly, sensor member 6 is configured to measure the magnitude, duration, a sensed or measured vibrational magnitude of pressure applicator 10 at dominant spectral frequencies, stroke frequency or rate, and/or angle of the force. More particularly, soft tissue mobilization system 2 is configured to measure and output data with respect to the magnitude (average, maximum, and minimum quantities) of the force applied to the soft tissue with soft tissue device 4, the duration or time (average, minimum, and maximum quantities) at which the force is applied to the soft tissue, the duration or time of an overall QSTM procedure with a patient, the frequency or rate (average, maximum, or minimum frequencies) at which a force is applied to the soft tissue based on the number of times force is applied to the soft tissue relative to a time period, the sensed vibrational magnitude at dominant spectral frequencies, and at least one angle measurement at which a force is applied to the soft tissue relative to the soft tissue or any other reference plane, point, or surface. In one embodiment, sensor member 6 may include a gyroscopic and/or accelerometer sensory member (not shown) to measure the angle and frequency of the force in three dimensions (X, Y, Z). Sensor member 6 also may have a built-in timer (not shown) to measure the duration of the force applied to the soft tissue. Sensor 6 also is configured to determine the position of pressure applicator 10, as disclosed herein.

An alternative embodiment of pressure applicator 10 (FIG. 7) is shown as pressure applicator 10' in FIG. 7A. Illustratively, pressure applicator 10' includes a first end 16' configured to extend from handle 12 and a second end 18' configured to be received within handle 12. Sensors 6 are positioned at the interface between second end 18' of pressure applicator 10' and handle 12 for real-time measurement of force applied to the soft tissue of a patient.

Figure 8:
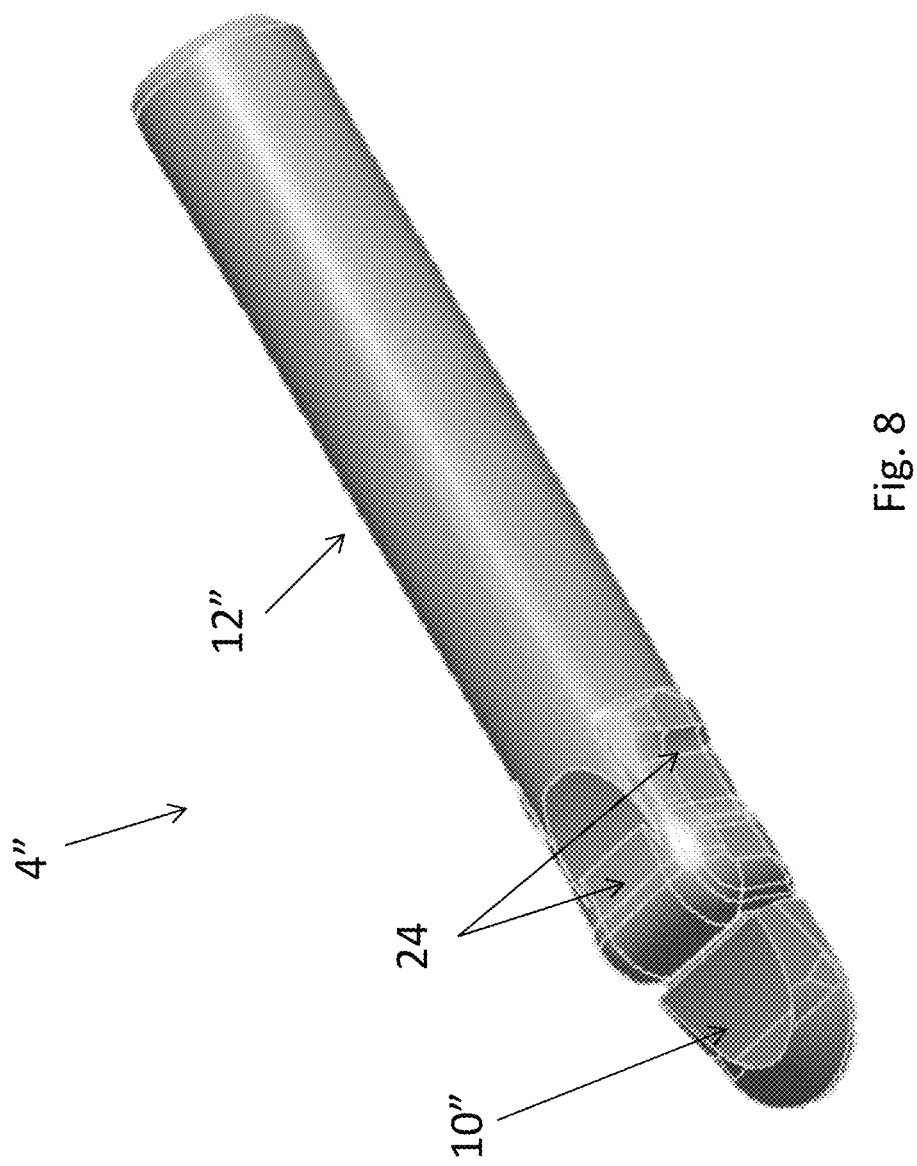
FIG. 8 is a perspective view of an alternative embodiment soft tissue device of the present disclosure.

An alternative embodiment of soft tissue device 4 (FIG. 2) is shown as soft tissue device 4" in FIG. 8. Illustratively, soft tissue device 4" includes a pressure applicator 10" and a handle 12". Handle 12" includes contour portions 24 which allow a doctor, clinician, therapist, or other professional to grip handle 12" when applying pressure to the patient's soft tissue through soft tissue device 4". Soft tissue device 4" operates at disclosed herein with respect to soft tissue device 4 by including sensors 6 (FIG. 7) at the interface between handle 12" and pressure applicator 10" such that the manual force applied by the doctor, therapist, clinician, or other professional is determined by sensor 6 to provide real-time feedback of the pressure parameters applied to the soft tissue of a patient via visual display 8.

Figure 9:
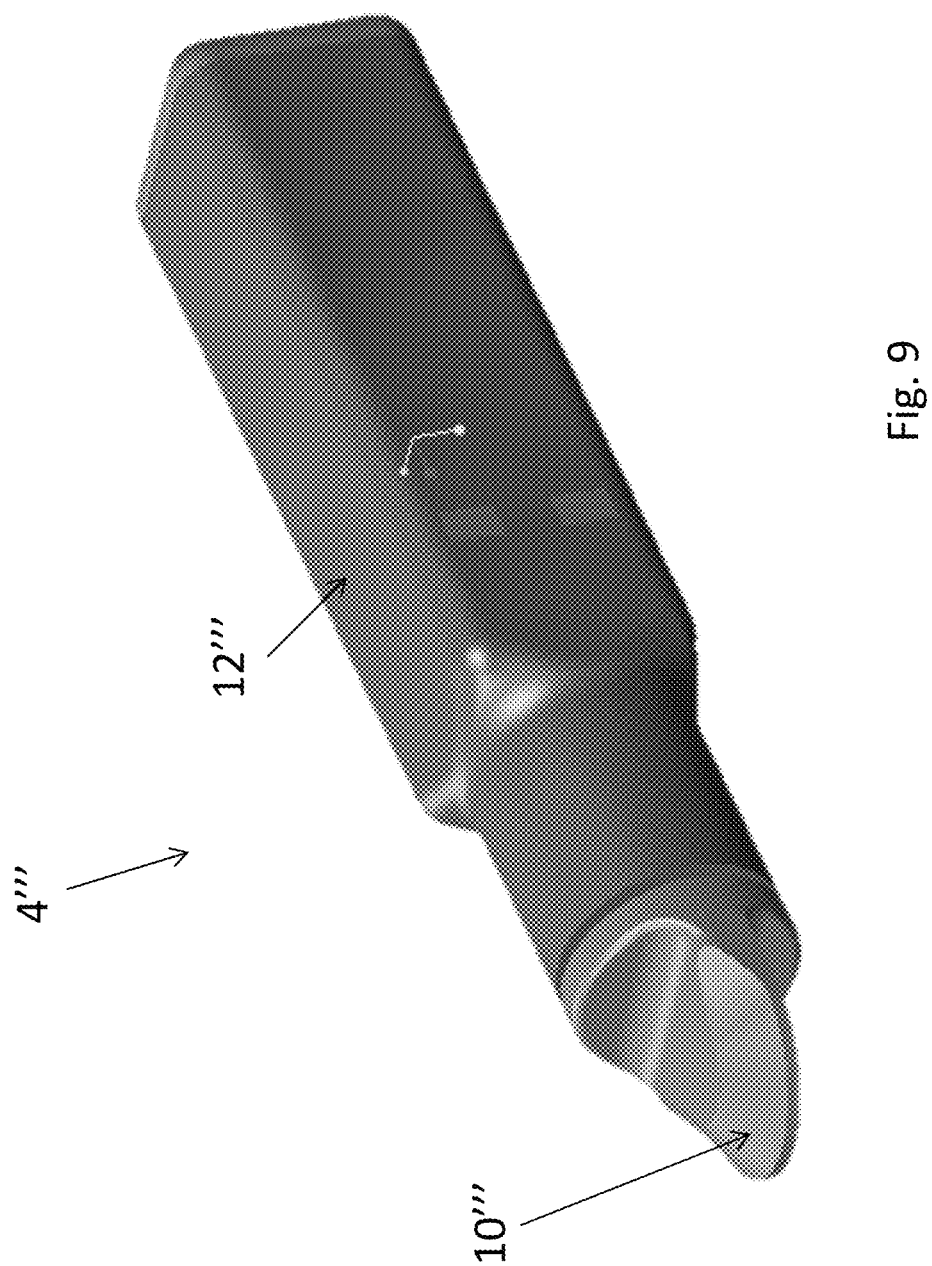
FIG. 9 is a perspective view of a further alternative embodiment soft tissue device of the present disclosure.

Similarly, a further alternative embodiment of soft tissue device 4 (FIG. 2) is shown as soft tissue device 4''' in FIG. 9. Illustratively, soft tissue device 4''' includes a pressure applicator 10''' and a handle 12'''. Soft tissue device 4''' operates at disclosed herein with respect to soft tissue device 4 by including sensors 6 (FIG. 7) at the interface between handle 12''' and pressure applicator 10''' such that the manual force applied by the doctor, therapist, clinician, or other professional is determined by sensor 6 to provide real-time feedback of the pressure parameters applied to the soft tissue of a patient via visual display 8.

Figure 10:
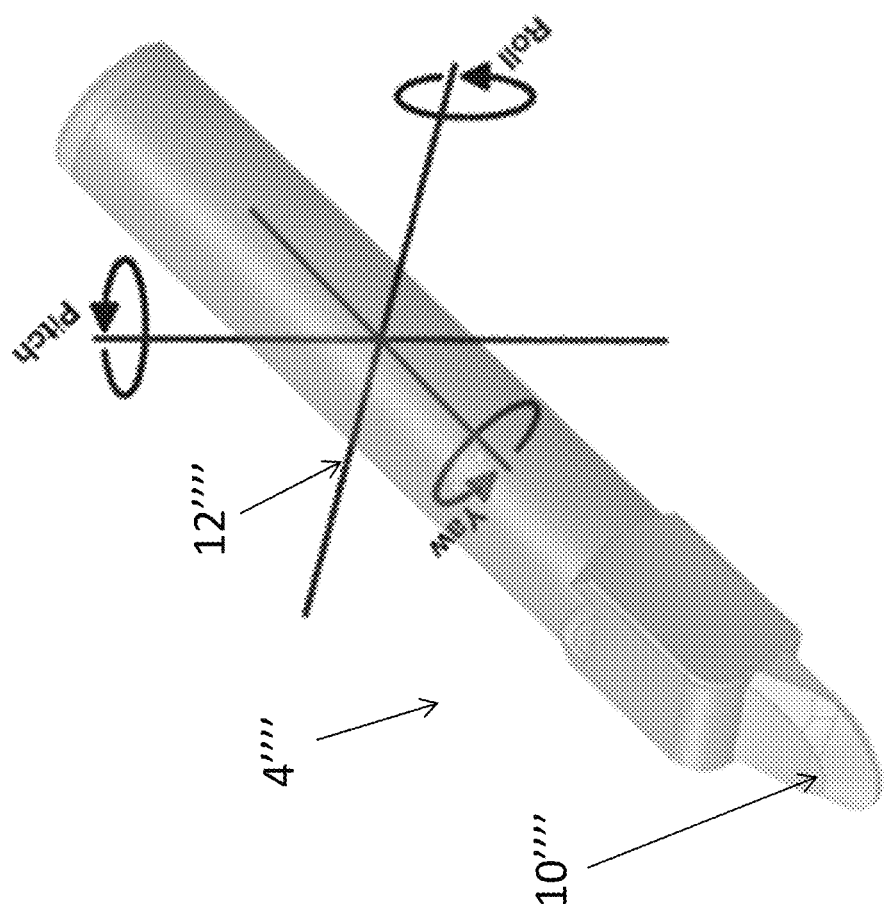
FIG. 10 is a perspective view of another alternative embodiment soft tissue device of the present disclosure.

Another alternative embodiment of soft tissue device 4 (FIG. 2) is shown as soft tissue device 4'''' in FIG. 10. Illustratively, soft tissue device 4'''' includes a pressure applicator 10'''' and a handle 12''''. Soft tissue device 4'''' operates at disclosed herein with respect to soft tissue device 4 by including sensors 6 (FIG. 7) at the interface between handle 12'''' and pressure applicator 10'''' such that the manual force applied by the doctor, therapist, clinician, or other professional is determined by sensor 6 to provide real-time feedback of the pressure parameters applied to the soft tissue of a patient via visual display 8.

In operation, a doctor, therapist, clinician, or professional places soft tissue device 4 on the soft tissue of a patient at a particular location of an injury or disease. As opposed to automated pressure mechanism, the doctor, therapist, clinician, or professional manually applies a force to handle 12 of soft tissue device 4 which transmits the force through soft tissue device 4 to apply pressure to the soft tissue of the patient. Sensor member 6 measures the magnitude, angle, yaw, pitch, roll, duration, and/or frequency of the force applied to handle 12 and wirelessly transmits the force data to visual display 8 in real time. As such, real time and three-dimensional force quantification data is displayed to the doctor, therapist, clinician, or professional administering the soft tissue massage.

Figure 12:
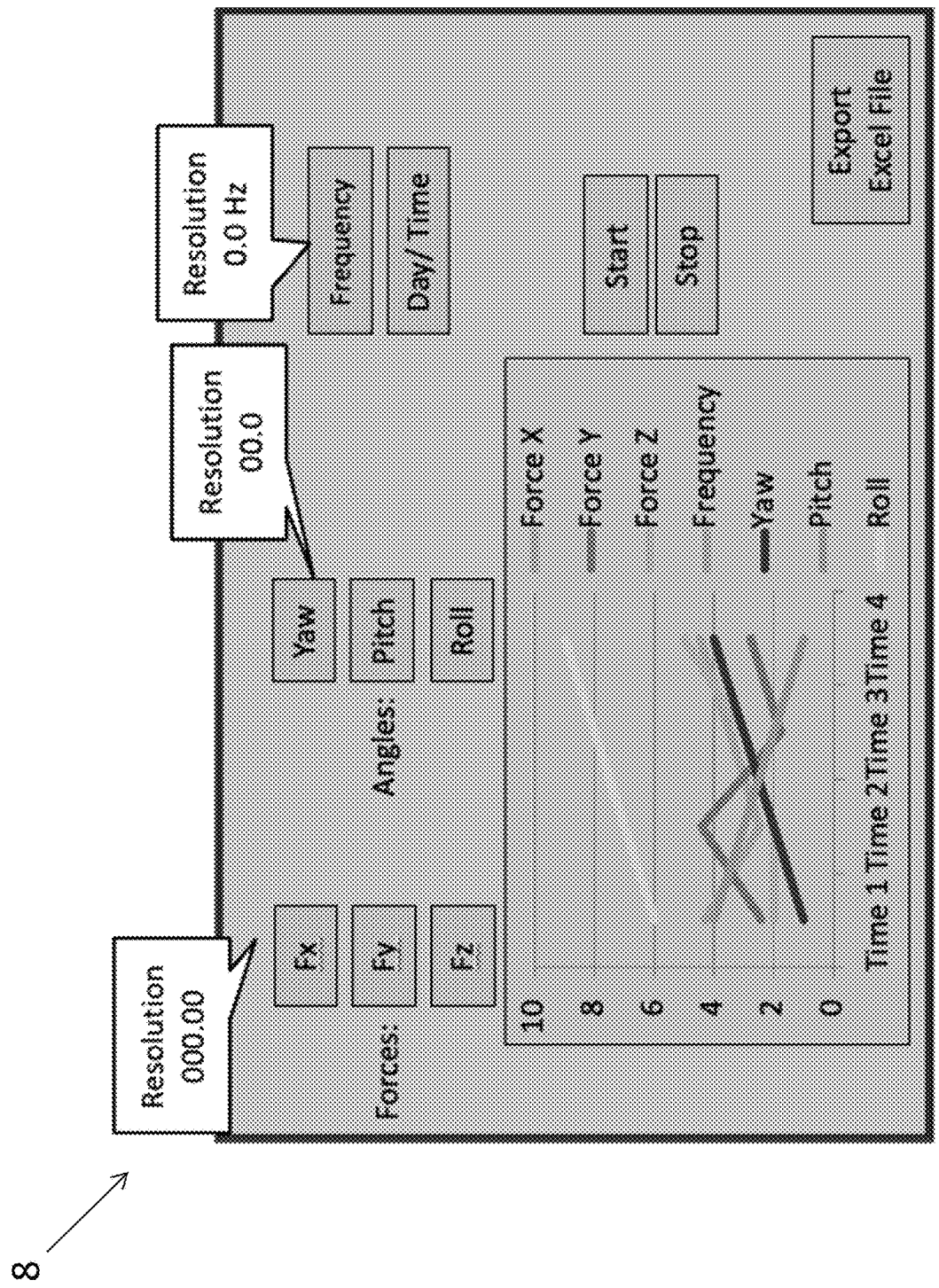
FIG. 12 is an embodiment of a visual display of the soft tissue mobilization system of FIG. 1.
Figure 13:
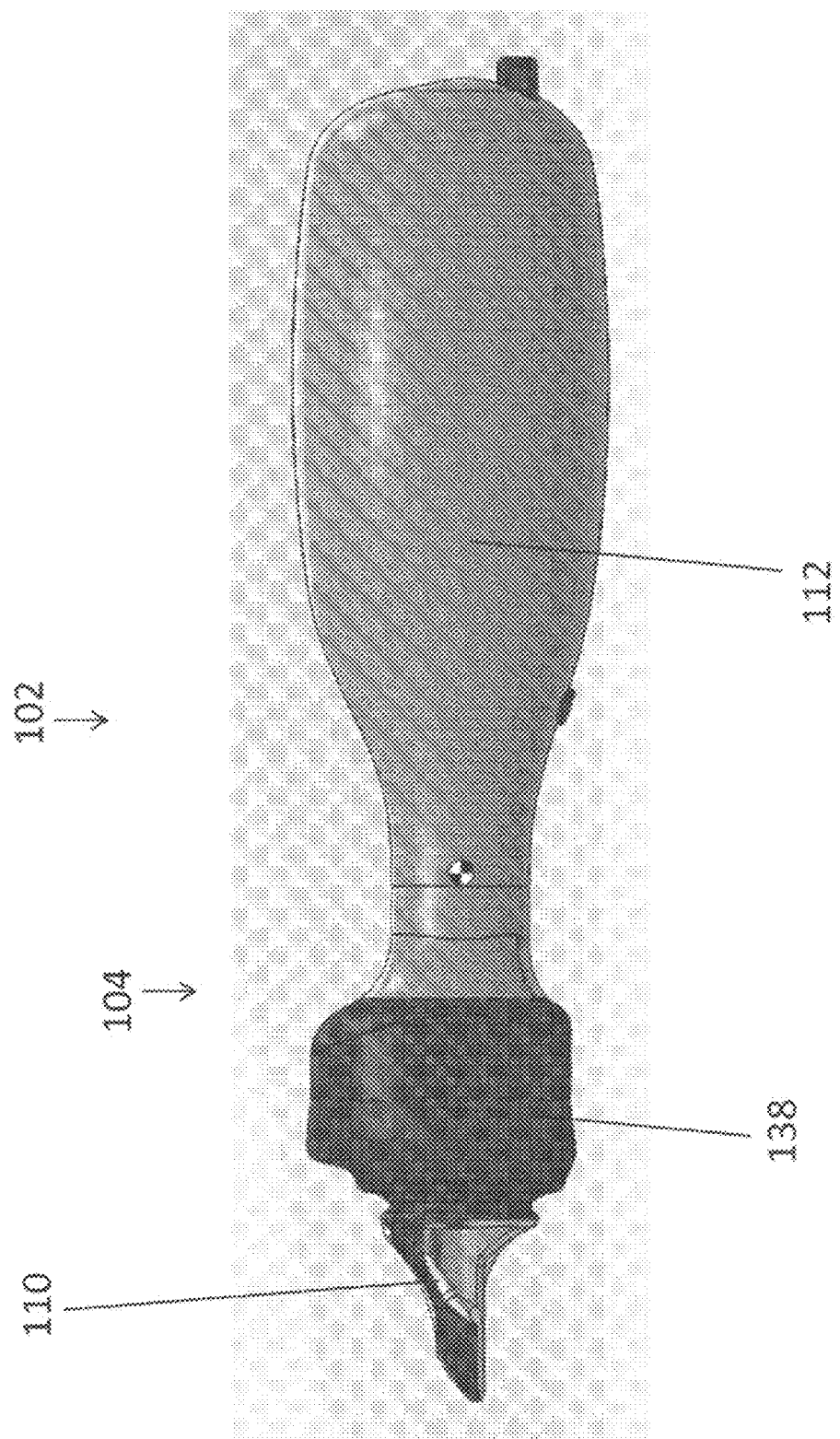
FIG. 13 is a side view of an alternative embodiment soft tissue mobilization system.

With this data, the doctor, therapist, clinician, or professional is able to monitor the force applied to the soft tissue such that the same force can be applied to the patient at a later time. For example, the real-time data may be displayed to the doctor, therapist, clinician, or professional on visual display 8, as shown in FIG. 12, such that force in all three (X, Y, Z) directions, the frequency of the force, and the angle (yaw, pitch, and roll) of the pressure applied to the soft tissue by soft tissue device 4 is shown on a graphical output to the doctor, therapist, clinician, or professional. Alternatively, visual display may show this data with a visual digital scale or graphic, a color-coded graphic with a first color (e.g., green) indicating light pressure, a second color (e.g., yellow) indicating the correct pressure, and a third color (e.g., red) indicating too much pressure, and/or a vector indicating the angle of the pressure. Additionally, an aural/audio indicator may be provided to the doctor, therapist, clinician, or professional (e.g., through earphones) to provide real-time data feedback regarding the pressure applied to the soft tissue and obviate the need for the doctor, therapist, clinician, or professional to look at visual display 8 when with the patient. The data measured by sensor 6 (FIG. 7) and relayed to visual display 8 via electronic assembly 14 may be stored for later review and/or export to a file. In this way, soft tissue mobilization system 2 can be used to provide consistent and replicable pressure to the patient during a massage-based therapy over the course of a treatment or therapy schedule. Additionally, guidelines, standards, and/or best practices can be created about the type of pressure which is most effective for particular injuries and/or diseases because real time force quantification is possible with soft tissue mobilization system 2.

Referring now to FIGS. 13-17, an alternative embodiment of soft tissue mobilization system 2 (FIG. 1) is shown as soft tissue mobilization system 102. The disclosure of soft tissue mobilization system 2, including any alternative embodiments disclosed herein, is relevant to soft tissue mobilization system 102, however, additional details of soft tissue mobilization system 102 are further described herein.

With respect to FIGS. 13-17, an alternative embodiment soft tissue device of soft tissue mobilization system 102 is shown as soft tissue device 104. Soft tissue device 104 is operably coupled to visual display 8 (FIG. 1) and is configured to quantify the pressure applied to the soft tissue of a patient during QSTM in real time. Illustratively, soft tissue device 104 includes a force sensor 106, a pressure applicator 110, a handle 112, and an electronics assembly 114 which includes force sensor 106, a power supply 108, a power management circuit 116, a calibration input 118, a power input 120, and a data acquisition unit 122.

As shown in FIG. 15, handle 112 may be comprised of two portions 112a, 112b which are coupled together to define handle 112. More particularly, handle portion 112a may include a lip 124 which is removably received within a portion of handle portion 112b to couple together portions 112a, 112b in a friction fit. Portions 112a, 112b also may be further coupled together with additional couplers, such as bolts, screws, adhesive, or any other type of fastener. Handle 112 may be comprised of a polymeric or metallic material, such as 3D printed plastic, stainless steel, or aluminum.

Handle 112 includes a plurality of internal openings or compartments to support various components of electronics assembly 114. For example, as shown in FIG. 15, handle 112 includes a first compartment 126 which is configured to support sensor 106. When sensor 106 is positioned within first compartment 126, sensor 106 is operably coupled to pressure applicator 110 through a pressure transmitter 128 (FIG. 14), illustratively a shaft or rod extending between pressure applicator 110 and sensor 106 through a channel 130 in handle 112. In this way, pressure applicator 110 applies a force to a patient's soft tissue, the force is measured by sensor 106 through pressure transmitter 128 and is further transmitted to visual display 8 (FIG. 1) via electronics assembly 114, as disclosed herein with respect to soft tissue mobilization system 2, 102 (FIG. 1).

Figure 14:
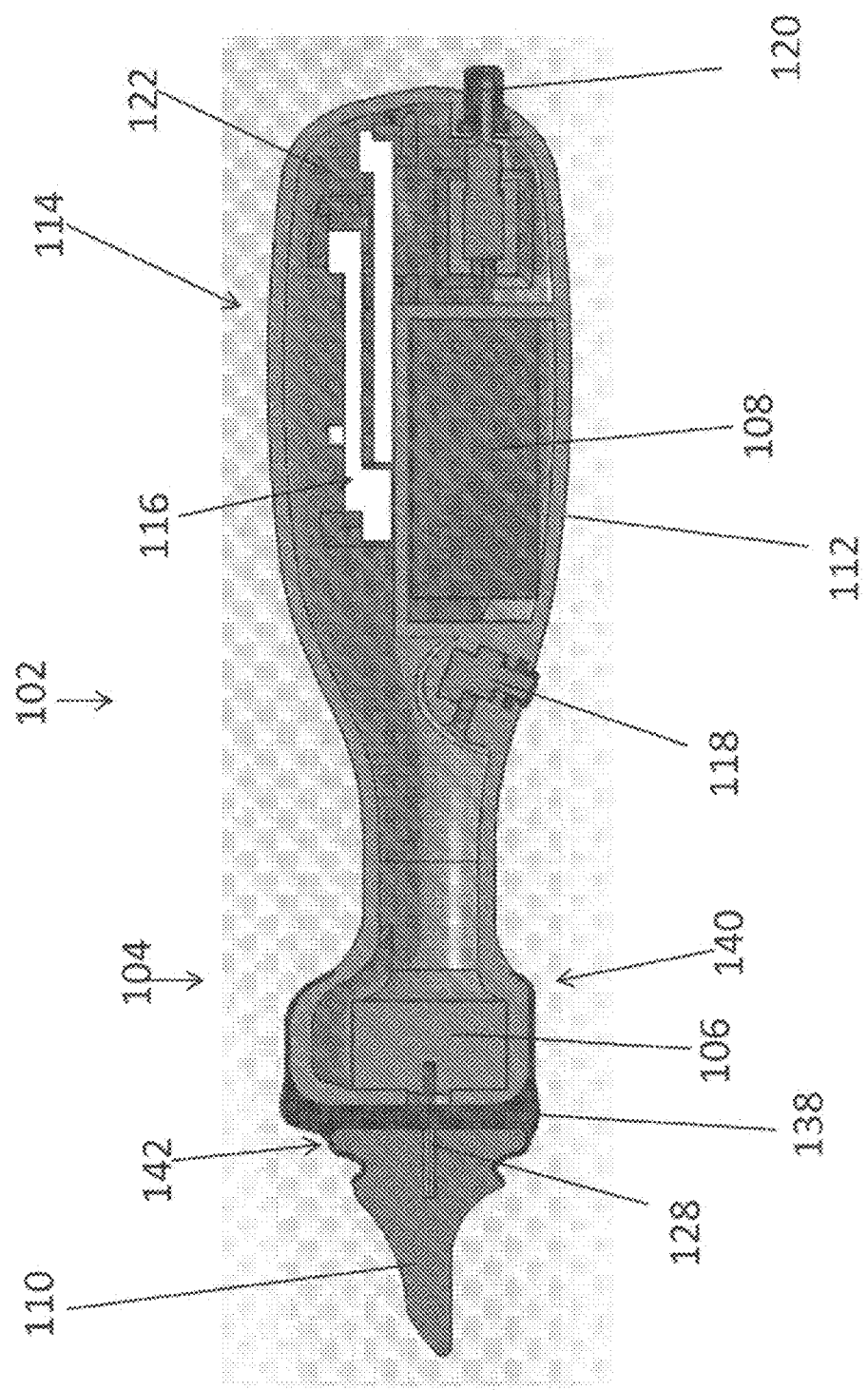
FIG. 14 is a cross-sectional view of the alternative soft tissue mobilization system of FIG. 13.
Figure 17:
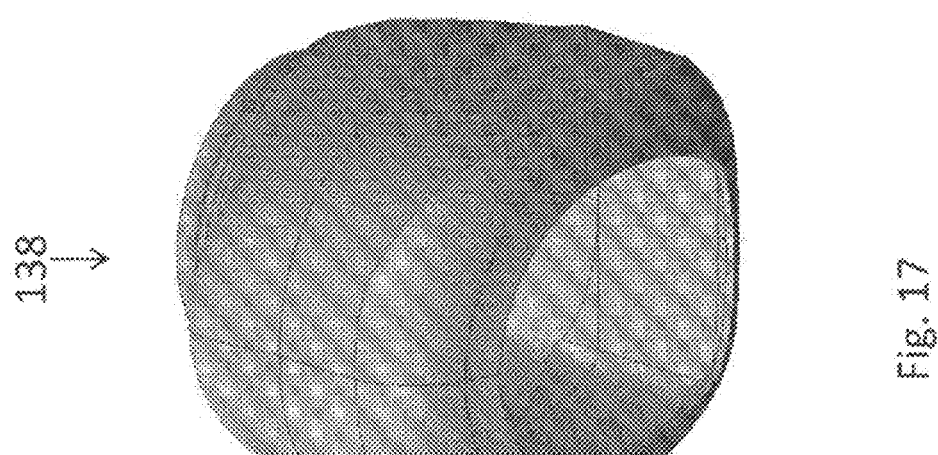
FIG. 17 is a front perspective view of an optional sealing member of the alternative soft tissue mobilization system of FIG. 13.
Figure 16:
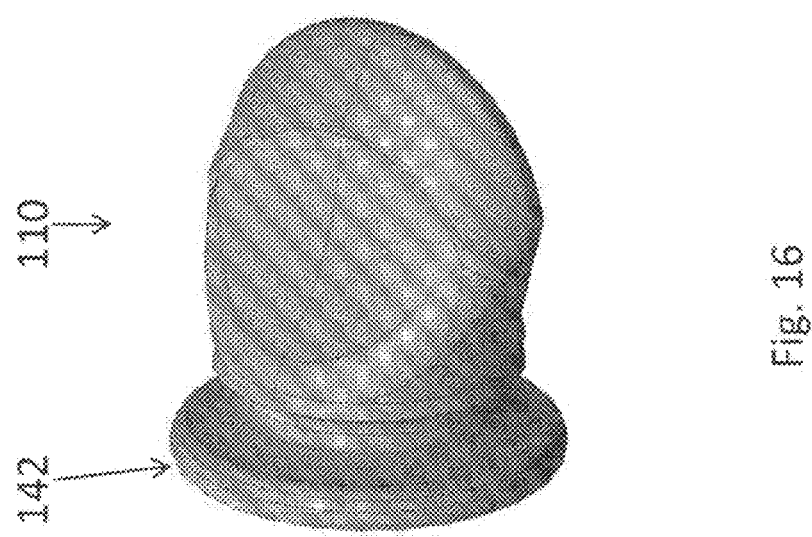
FIG. 16 is a side perspective view of a pressure applicator of the alternative soft tissue mobilization system of FIG. 13.

Handle 112 also includes a second compartment 132 configured to receive calibration input 118. Illustratively, as shown in FIG. 14, calibration input 118 may be a mechanical or electrical switch (e.g., a push button) configured to receive an input from a user to initiate a calibration or "reset" process prior to each individual use of soft tissue device 4, 104, if necessary. Handle 112 further includes a third compartment 134 configured to support both power management circuit 116 and data acquisition unit 122. Handle 112 also includes a fourth compartment 136 configured to receive power input 120. Illustratively, as shown in FIG. 14, power input 120 may be a mechanical or electrical switch (e.g., a push button) configured to receive an input from a user to turn soft tissue device 4 on and off. Additionally, handle 112 includes a fifth compartment 139 configured to receive power supply 108. Power supply 108 is illustratively disclosed as a battery, however, power supply 108 may be any other type of source configured to provide power to soft tissue device 104.

As shown in FIGS. 13, 14, 16, and 17, pressure applicator 110 is removably coupled to handle 112 with a sealing member 138. Illustratively, sealing member 138 is a sleeve or grommet configured to inhibit fluids from entering handle 112 through channel 130 and defines a waterproof member. As shown in FIG. 14, sealing member 138 is configured to extend around a forward portion 140 of handle 112 and also extends around a rearward portion 142 of pressure applicator 110. Sealing member 138 also may be configured to extend longitudinally between rearward end 142 of pressure applicator 110 and forward portion 140 of handle 112.

Figure 18:
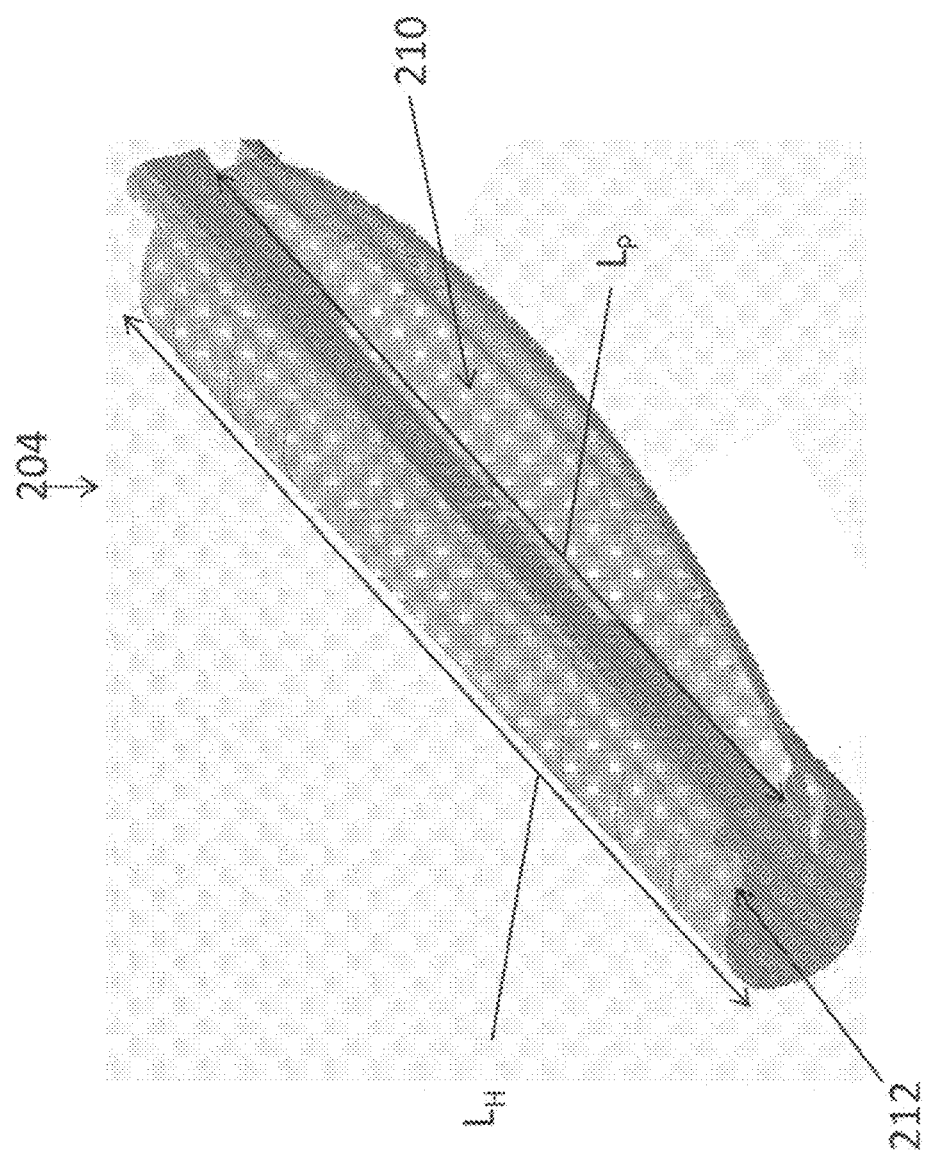
FIG. 18 is a front perspective view of a further alternative embodiment soft tissue mobilization system.
Figure 19:
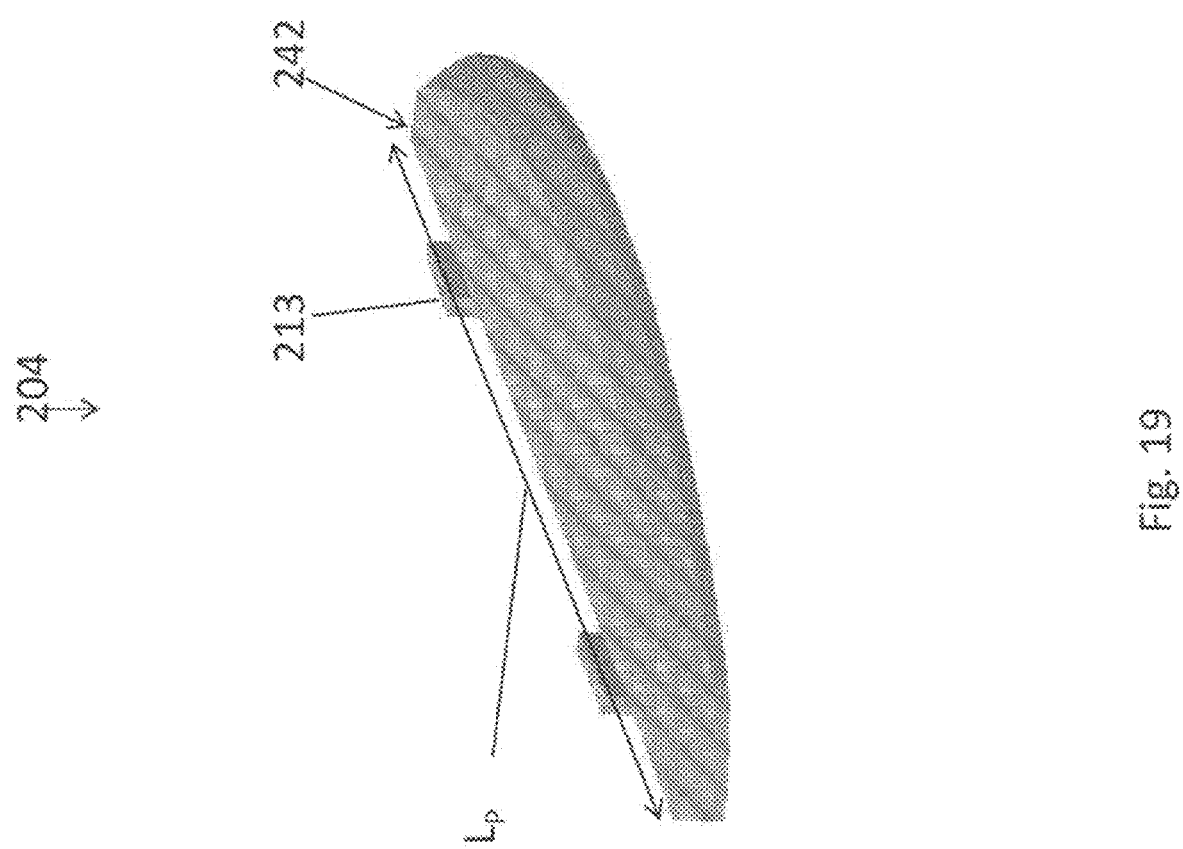
FIG. 19 is a front perspective view of a pressure applicator of the soft tissue mobilization system of FIG. 19.

Referring to FIGS. 18 and 19, a further embodiment of soft tissue mobilization system 102 includes a soft tissue device 204. Soft tissue device 204 includes a pressure applicator 210 and a handle 212. Pressure applicator 210 has a length $L_P$ which is generally equal to a length $L_H$ of handle 112. In this way, pressure applicator 210 has a larger surface area for contacting the patient's soft tissue compared to pressure applicator 10, 110. As such, pressure applicator 210 is configured to evenly apply or disperse pressure to the patient's soft tissue in contact with pressure applicator 210 over a larger area of the soft tissue than pressure applicators 10, 110. As shown in FIG. 19, pressure applicator 210 includes tabs 213 extending at a rear end 242 for coupling within handle 212. More particularly, handle 212 is configured to receive tabs 213 such that pressure applicator 210 is mechanically and frictionally retained within handle 212. Although not shown, handle 112 may include internal compartments as with handle 112 for supporting sensor 106 and electronics assembly 114 (FIG. 14).

Figure 20:
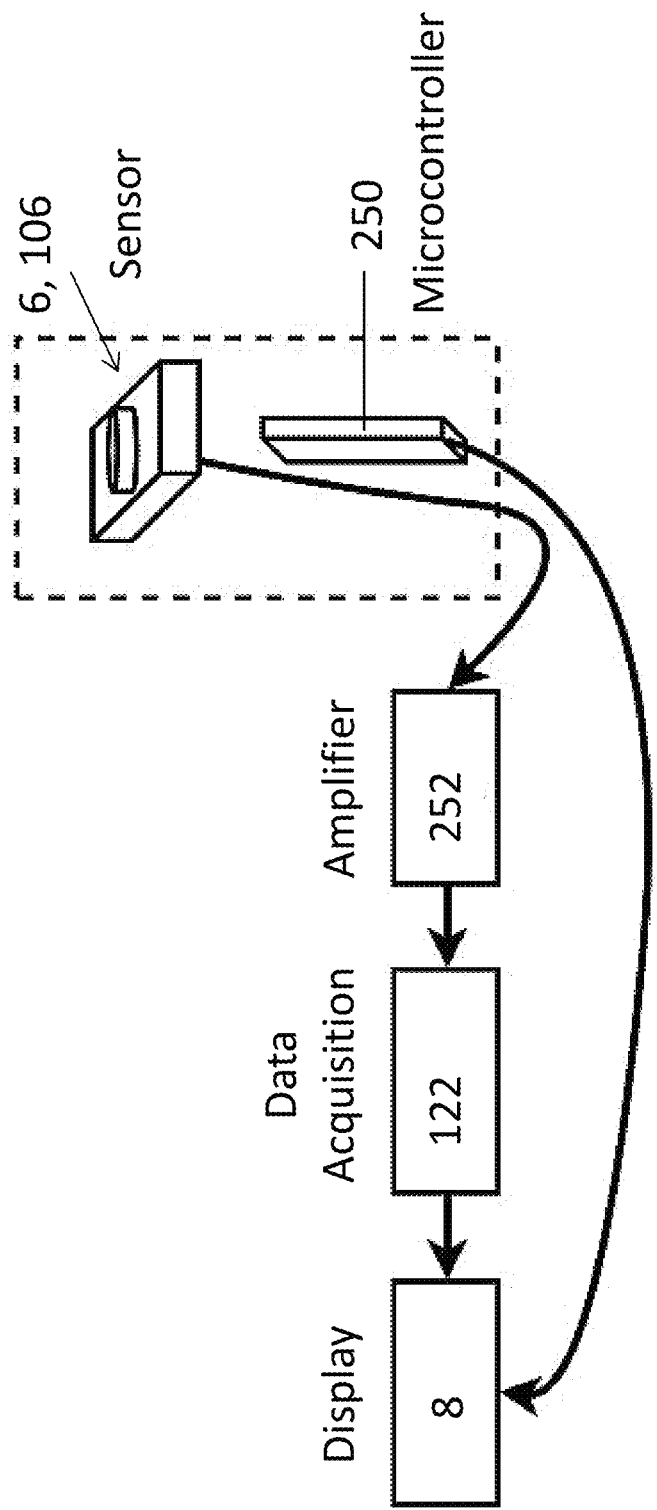
FIG. 20 is a schematic view of an electronics assembly configured to be used with the soft tissue mobilization system.

Any of soft tissue devices 4, 104, 204 may be configured to operate with electronics assembly 14, 114, as disclosed herein. More particularly, with respect to FIG. 20, electronics assembly 14, 114 is operably coupled to and/or supported by soft tissue device 4, 104, 204. More particularly, sensor 6, 106 may be supported within a portion of soft tissue device 4, 104, 204, as disclosed herein. Additionally, soft tissue device 4, 104, 204 also may support a microcontroller 250 operably coupled to visual display 8.

Figure 21:
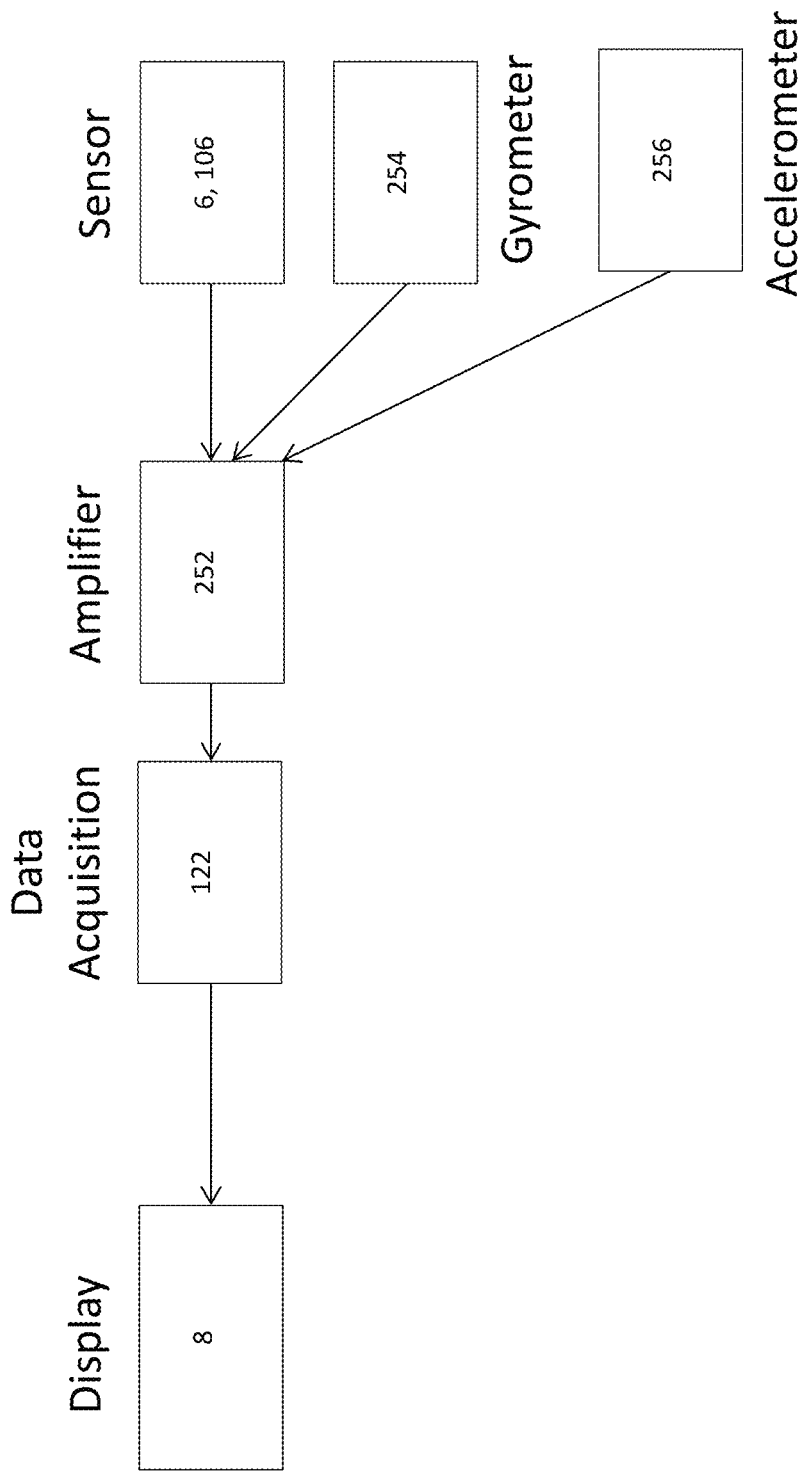
FIG. 21 is a schematic view of an alternative electronics assembly configured to be used with the soft tissue mobilization system.

Electronics assembly 14, 114 also includes data acquisition unit 122 which is operably coupled to an amplifier 252. More particularly, amplifier 252 operably couples data acquisition unit 122 to sensor 6, 106 on soft tissue device 4, 104, 204. In one embodiment, as shown in FIG. 21, amplifier 252 may include more than one amplification device configured to provide data to data acquisition unit 122. For example, amplifier 252 may include an inertial measurement unit (IMU) having a gyrometer 254 to measure angular speed of pressure applicator 10, 110, 210 when applied to the patient's soft tissue. Additionally, amplifier 252 may include an IMU having an accelerometer 256 to measure acceleration which, in conjunction with 3D angular speed information, can be used to estimate the orientation and position of soft tissue device 4, 104, 204 relative to the patient's soft tissue.

In operation, soft tissue mobilization system 2, 102 is configured to apply a force to a patient's soft tissue and quantify the force in real time. In this way, soft tissue mobilization system 2, 102 is configured to provide real-time data to the doctor, nurse, therapist, or other professional administering pressure to the patient's soft tissue during QSTM. This allows for consistent therapy for the patient because the pressure applied to various portions of the patient's skin may be quantified, stored or otherwise documented, and reproduced during subsequent therapy sessions.

During a therapy session or appointment, a doctor, nurse, therapist, or other professional ensures soft tissue device 4, 104, 204 is powered on and/or otherwise actively connected to electronics assembly 14, 114 through a wired or wireless connection. The doctor, nurse, therapist, or other professional then contacts the patient's soft tissue with pressure applicator 10, 110, 210 and applies a force to soft tissue device 4, 104, 204 which is then transferred to the patient's soft tissue through pressure applicator 10, 110, 210. The force applied to the patient's soft tissue is measured or otherwise sensed by sensor 6, 106 and the force data is transmitted to data acquisition unit 122. Data acquisition unit 122 may include a receiver and transmitter (not shown) such that data acquisition unit 122 receives the data from sensor 6, 106 and amplifier(s) 250 and also transmits the data to visual display 8 to visually output the magnitude, stroke, frequency, duration, position, and/or angle of the force applied to the patient's skin to the doctor, nurse, therapist, or other professional.

Data acquisition unit 122 also is configured to receive and transmit data from amplifier 250 such that data related to the orientation and/or position of pressure applicator 10, 110, 210 (e.g., in the X, Y, and Z axes on a coordinate system) and the angular speed of pressure applicator 10, 110, 210 also is transmitted to visual display 8. In this way, electronics assembly 14, 114 is configured to measure and output the force applied to the patient's soft tissue in real time during a therapy or other appointment with the patient. As such, this data may be recorded and stored within electronics assembly 14, 114 and/or the computing device, for example in a memory of the computing device associated with visual display 8, such that a patient's treatment record, therapy log or plan, or other medical notes may be updated and retrieved for subsequent appointments with the patient. By measuring and recording the use of soft tissue device 4, 104, 204 during QSTM with a patient, the same force can be consistently applied to the patient's soft tissue for consistent and reproducible therapy procedures.

Figure 22:
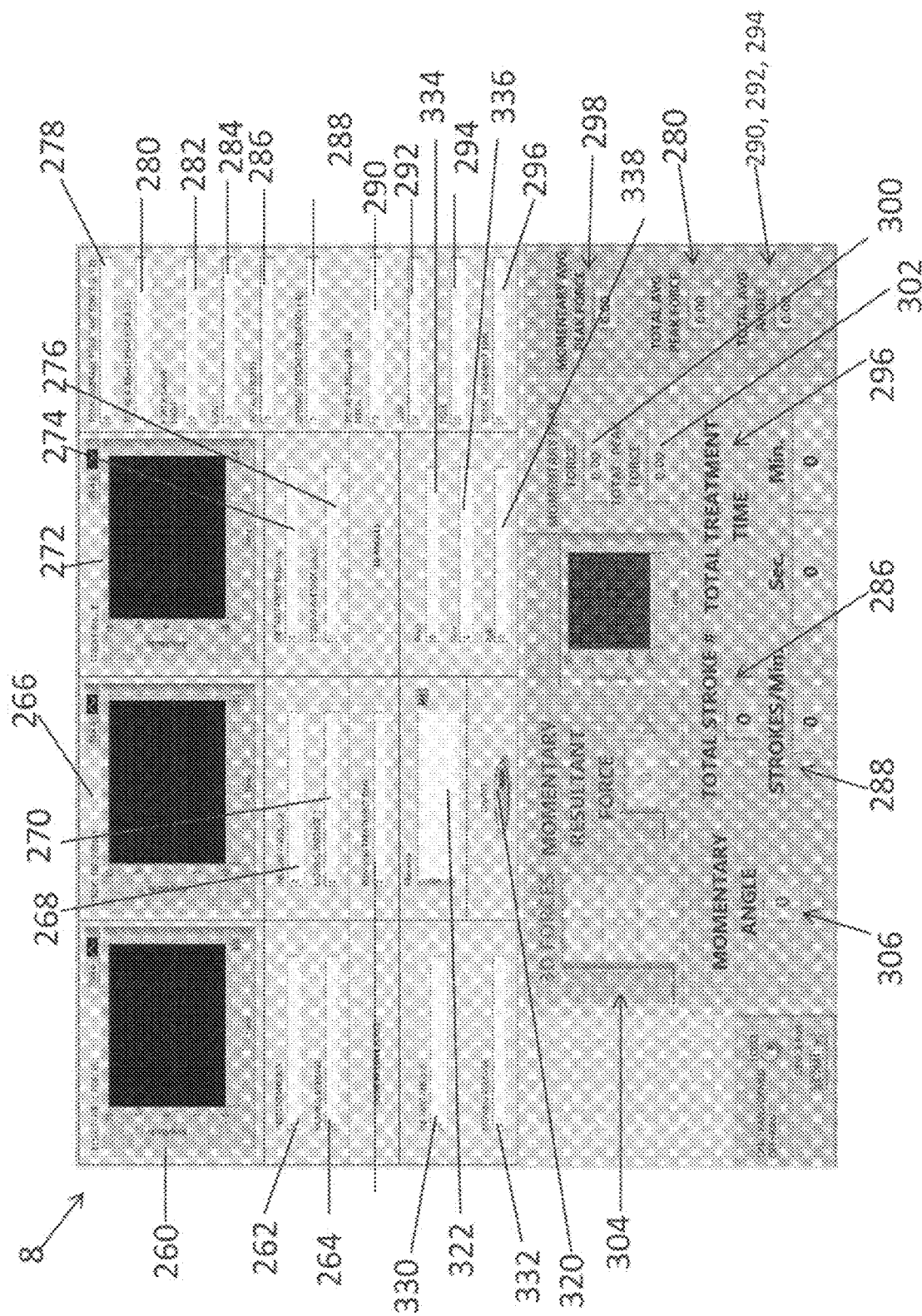
FIG. 22 is an embodiment of a user interface displayed on a visual display of the soft tissue mobilization system during a massage-based therapy.

As shown in FIG. 22, in one embodiment, visual display 8 (FIG. 1) is configured to output at least one display screen which provides the doctor, nurse, therapist, or other professional with various data related to the use of pressure applicator 10, 110, 210 on the patient's soft tissue. For example, visual display 8 may graphically and/or numerically display data related to resultant 3D forces, stroke frequency of pressure applicator 10, 110, 210, the stroke angle of pressure applicator 10, 110, 210, the momentary and total peak force, the momentary angle, and the total treatment time. More particularly, as shown in FIG. 22, visual display 8 outputs the following real-time data during a QSTM appointment with a patient: Amplitude vs. Time Resultant 3D Force 260, Instantaneous Resultant 3D Force 262, Moving Average Resultant 3D Force 264, Amplitude vs. Time Stroke Frequency 266, Instantaneous Stroke Frequency 268, Moving Average Stroke Frequency 270, Amplitude vs. Time Stroke Angle 272, Instantaneous Stroke Angle 274, Moving Average Stroke Angle 276, Total Average Resultant Force (X, Y, Z) 278, Total Average Peak Force (Z) 280, Maximum Force Range 282, Minimum Force Range 284, Total Strokes 286, Average Stroke Frequency (Hz) 288, Total Average Angle Pitch 290, Yaw 292, Roll 294, Total Treatment Time 296, Momentary Average Peak Force 298, Momentary Peak Force 300, Total Peak Force 302, 3D Forces/Momentary Resultant Force 304, Instantaneous Compressive Force 330, Moving Average Compressive Force 332, 3D Angle Pitch 334, 3D Angle Yaw 336, 3D Angle Roll 338, and/or Momentary Angle 306. Visual display 8 and/or the computing device may also include a power input 320 turning display 8 and/or the computing device on and off and a filename input 322 for storing the data from a QSTM session. In this way, visual display 8 allows for quantification of maximum and minimum forces applied to the patient's soft tissue, average forces applied to the patient's soft tissue, the number of times a force was applied to the patient's soft tissue, and the duration of time a force is applied to the patient's soft tissue which allows for various rates of force and frequency of force to be determined, such as an average rate of force or an average frequency of force. Visual display 8 also allows for the orientation angle, including pitch, yaw, and roll, to be measured, observed, and/or recorded such that the stroke position and the orientation of pressure applicator 10, 110, 210 may be observed.

In one embodiment, visual display 8 may be configured to allow a doctor, nurse, therapist, clinician, or other professional to start at a single location on the patient's soft tissue and move pressure applicator 10, 110, 210 in systematic and continuous motion to "map" the patient's soft tissue in a particular area of the body. Such data is recorded using electronics assembly 14, 114 and may be displayed on visual display 8. In this way, soft tissue mobilization system 2, 102 is configured to provide electronic feedback of the soft tissue as a way for the doctor, nurse, clinician, therapist, or other professional to characterize the health of the soft tissue. For example, healthy the soft tissue may feel like smooth sheets of paper such that soft tissue device 4, 104, 204 easily glides over the soft tissue. Conversely, unhealthy, damaged, or aged soft tissue may feel like crumpled paper such that pressure applicator 10, 110, 210 records bumps, creases, or other uneven tone or surface dimensions of the soft tissue. This information is transmitted to visual display 8 to essentially provide a topographical "map" of the patient's soft tissue in a particular area which allows for the health of the soft tissue to be evaluated. In one embodiment, visual display 8 is configured to provide a pictorial image of the patient's soft tissue.

Figure 23:
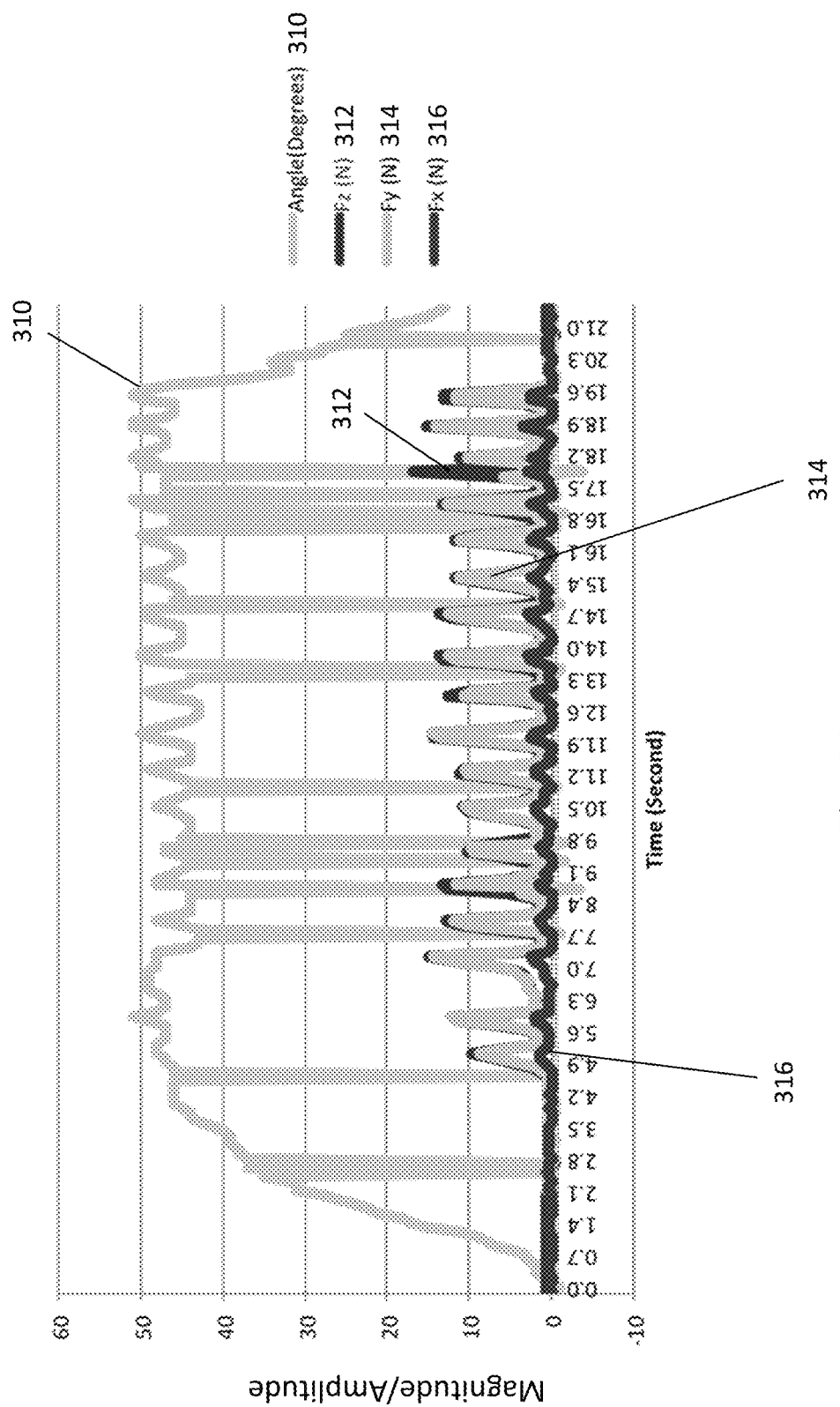
FIG. 23 is an example of data that may be obtained with the soft tissue mobilization system.

Referring to FIG. 23, soft tissue mobilization system 2, 102 may be further configured to generate, display, or otherwise output a graph or other visual indicator of the results obtained by soft tissue device 4, 104, 204. For example, a graphical output may be provided to the doctor, nurse, therapist, or other professional to further indicate the results of the QSTM with the patient. In one embodiment, a graphical output may be provided in real time to show the magnitude or amplitude of the angle 310 of pressure applicator 10, 110, 210 and the force 312, 314, 316 (in Newtons) in the respective Z, Y, and X axes of pressure applicator 10, 110, 210 relative to the treatment time.

Before, during, or after an appointment with a patient, the force data measured by sensor 6, 106 may undergo a transformation calculation or process using software on the computing device for visual display 8. More particularly, in one example of using soft tissue device 4, 104, 204, soft tissue device 4, 104, 204 may have three different coordinate systems for three different components thereof (illustrated in FIG. 33): (1) microprocessor 250; (2) sensor 6, 106; and (3) pressure applicator 10, 110, 210. Sensor 6, 106 and microcontroller 250 coordinates are based on external datasheets available from the manufacturer or other external source and pressure applicator 10, 110, 210 coordinates have the following sign convention: +Y when soft tissue device 4, 104, 204 moves forward, +X when soft tissue device 4, 104, 204 moves to the right, and +Z when soft tissue device 4, 104, 204 moves upwardly. This sign convention is based on the Right-Hand Rule.

Figure 34:
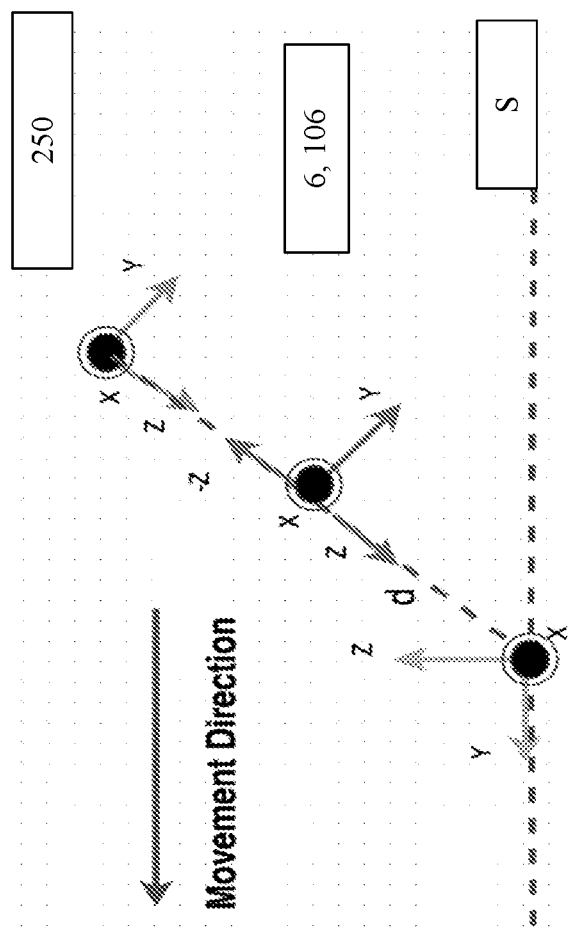
FIG. 34 is another diagram view of different coordinate systems for different components of the soft tissue mobilization system.

During QSTM, the force applied to patient's soft tissue S is measured and the measured force data undergoes a transformation. To perform the force transformation, the coordinate of microcontroller 250 is rotated approximately 90 degrees counterclockwise about the X-axis to align or otherwise agree with the orientation of the coordinate of sensor 6, 106, as shown in FIG. 34. Next, the orientation angles are used to transfer the force measurement to the coordinate system of soft tissue S because microcontroller 250 and sensor 6, 106 coordinates agree with each other, as both coordinates are on the same solid body.

Based on Euler's Rotation Theorem, any arbitrary rotation for a solid object or vector (V) can be represented by a combination of three rotations, as shown in Equation (1), $$V = ROTx \times ROTy \times ROTz \times V \quad (1)$$

where rotations about the X, Y, and Z axes are computed using Equations (2)-(4). All angles may be multiplied by (−1) to allow the force components to transfer back to the origin (horizontal plane) of the coordinate of sensor 6, 106 after any rotation in 3D space.

$$ROTx = \begin{bmatrix} 1 & 0 & 0 & 0 \\ 0 & \cos d(-p) & -\sin d(-p) & 0 \\ 0 & \sin d(-p) & \cos d(-p) & 0 \\ 0 & 0 & 0 & 1 \end{bmatrix} \quad (2)$$

$$ROTy = \begin{bmatrix} \cos d(-r) & 0 & \sin d(-r) & 0 \\ 0 & 1 & 0 & 0 \\ -\sin d(-r) & 0 & \cos d(-r) & 0 \\ 0 & 0 & 0 & 1 \end{bmatrix} \quad (3)$$

$$ROTz = \begin{bmatrix} \cos d(-y) & -\sin d(-y) & 0 & 0 \\ \sin d(-y) & \cos d(-y) & 0 & 0 \\ 0 & 0 & 1 & 0 \\ 0 & 0 & 0 & 1 \end{bmatrix} \quad (4)$$

Next, measurements may be transferred to soft tissue S with a distance d, which is the distance between the measuring point on sensor 6, 106 and pressure applicator 10, 110, 210, and is represented in matrix form, as shown in Equation (5).

$$T = \begin{bmatrix} 1 & 0 & 0 & 0 \\ 0 & 1 & 0 & 0 \\ 0 & 0 & 1 & d \\ 0 & 0 & 0 & 1 \end{bmatrix} \quad (5)$$

Then, a counterclockwise rotation about the X-axis may be performed to transfer the measurements to the proposed practice direction, as shown in Equation (6). Equation (6) may be used to transfer the force measurement to the coordinate of soft tissue S.

$$ROTx - \text{skin} = \begin{bmatrix} 1 & 0 & 0 & 0 \\ 0 & \cos d(90) & -\sin d(90) & 0 \\ 0 & \sin d(90) & \cos d(90) & 0 \\ 0 & 0 & 0 & 1 \end{bmatrix} \quad (6)$$

Finally, to obtain the transformed force measurement on soft tissue S, the force vector may be multiplied by the distance matrix, Euler's rotation matrix, and the assumed practice direction matrix, respectively, as shown in Equation (7).

$$F' = ROTx_{skin} \times ROTx \times ROTy \times ROTz \times T \times F \quad (7)$$

Equation (7) may be computed using MATLAB or another computer program, to represent each force component in a separate formula, as shown in Equations (8), (9), and (10).

$$Fx' = d \times \sin d(-r) + Fz \times \sin d(-r) + Fx \times \cos d(-r) \times \cos d(-y) - Fy \cos d(-r) \times \sin d(-y) \quad (8)$$

$$Fy' = \times Fx \times (\sin d(-p) \times \sin d(-y) - \cos d(-p) \times \cos d(-y) \times \sin d(-r)) - Fy \times (\cos d(-y) \times \sin d(-r) + \cos d(-p) \times \sin d(-r) \times \sin d(-y)) - Fz \times \cos d(-p) \times \cos d(-r) - d \times \cos d(-p) \times \cos d(-r) \quad (9)$$

$$Fz' = Fx \times (\cos d(-p) \times \sin d(-y) + \cos d(-y) \times \sin d(-p) \times \sin d(-r)) + Fy \times (\cos d(-p) \times \cos d(-y) - \sin d(-p) \times \sin d(-r) \times \sin d(-y)) - Fz \times \cos d(-r) \times \sin d(-p) - d \times \cos d(-r) \times \sin d(-p) \quad (10)$$

The force transformation described above is based on a fixed gravitational coordinate system and is accurate when the soft tissue coordinate system aligns with the gravitational reference. In order to ensure that the transformed forces are accurate even when the skin coordinate system is not aligned with the gravitational frame, soft tissue device 4, 104, 204 is first aligned with soft tissue S where treatment will be performed. Calibration input 118 on soft tissue device 4, 104, 204 is then actuated by the doctor, nurse, or therapist to confirm the alignment. Actuating calibration input 118 triggers software of the computing device associated with visual display 8 to record the 3D orientation angles of soft tissue device 4, 104, 204, thereby establishing the skin coordinate system with respect to the gravitational frame. These angles are then used to obtain the 3D orientation angles of soft tissue device 4, 104, 204 with respect to skin coordinate system which are subsequently used in the force transformation equations.

Figure 24:
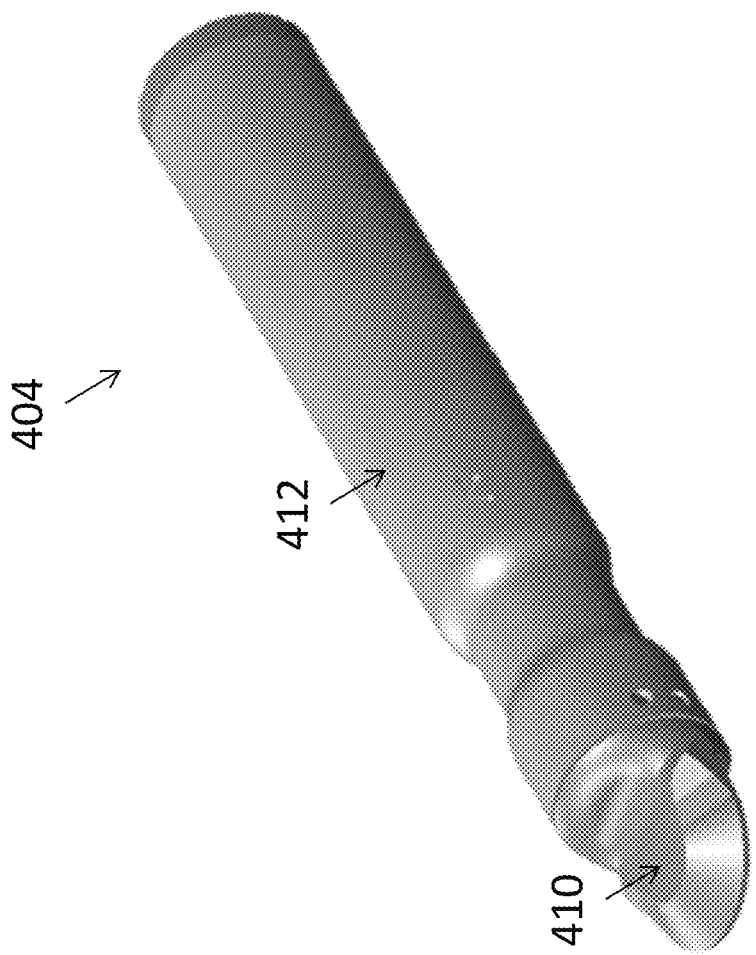
FIG. 24 is a front perspective view of an alternative embodiment soft tissue device.
Figure 25:
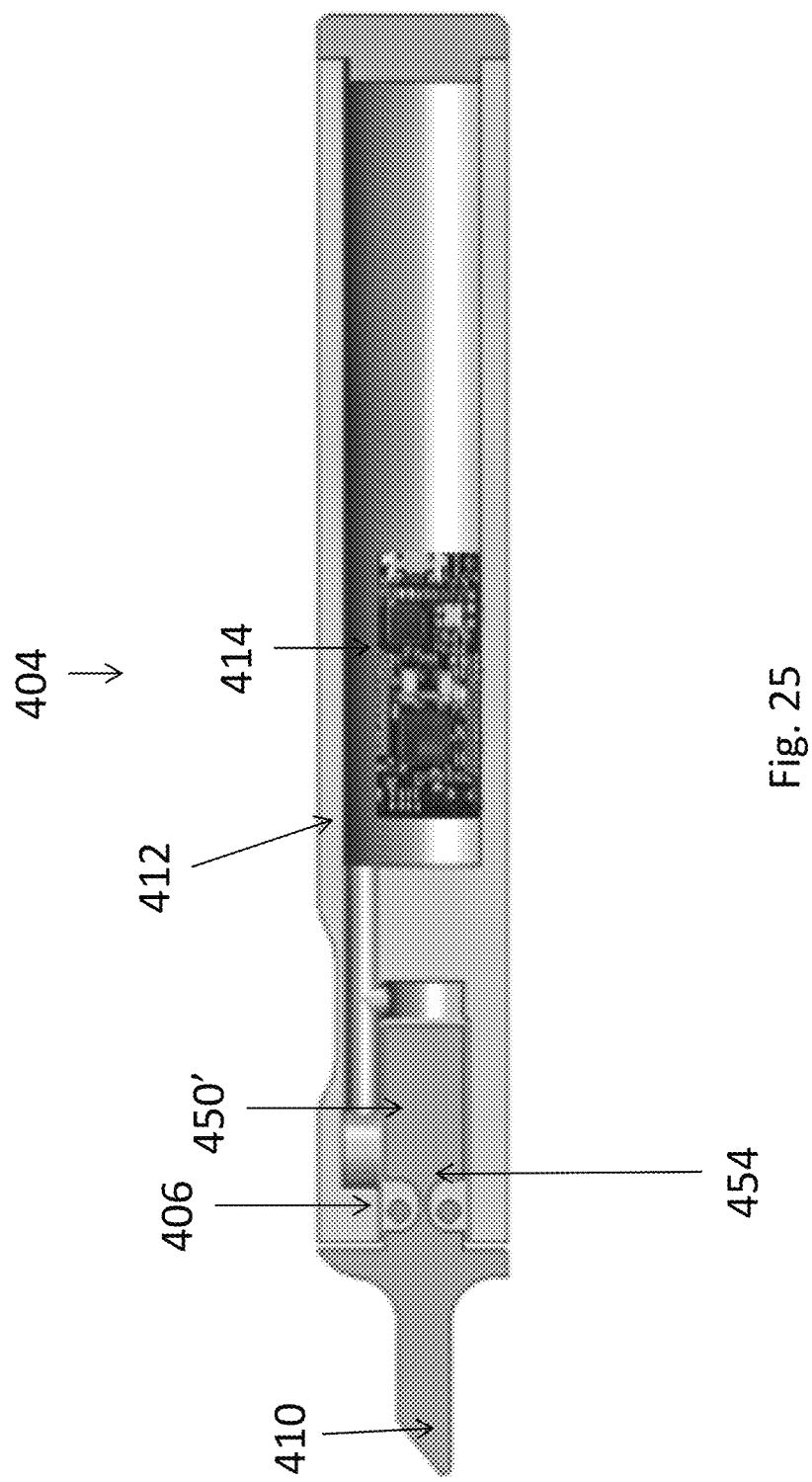
FIG. 25 is a cross-sectional view of the soft tissue device of FIG. 24.
Figure 26:
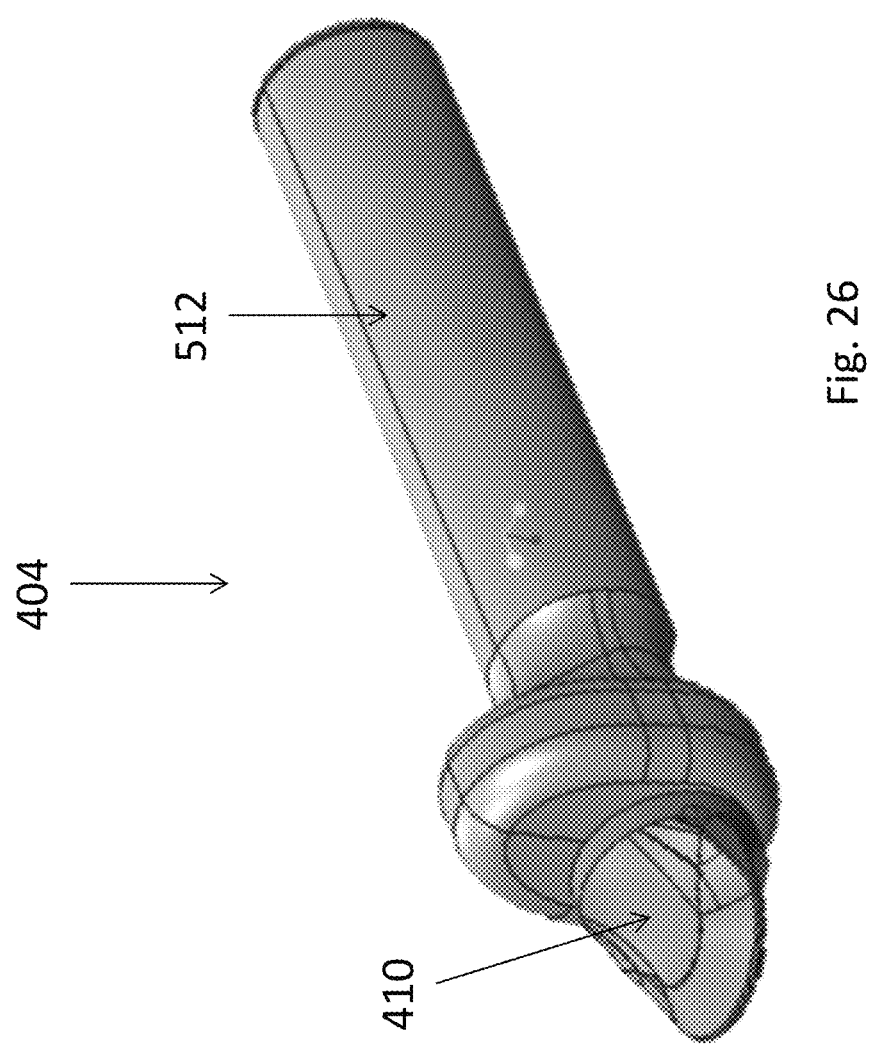
FIG. 26 is a front perspective view of a further alternative embodiment soft tissue device.
Figure 27:
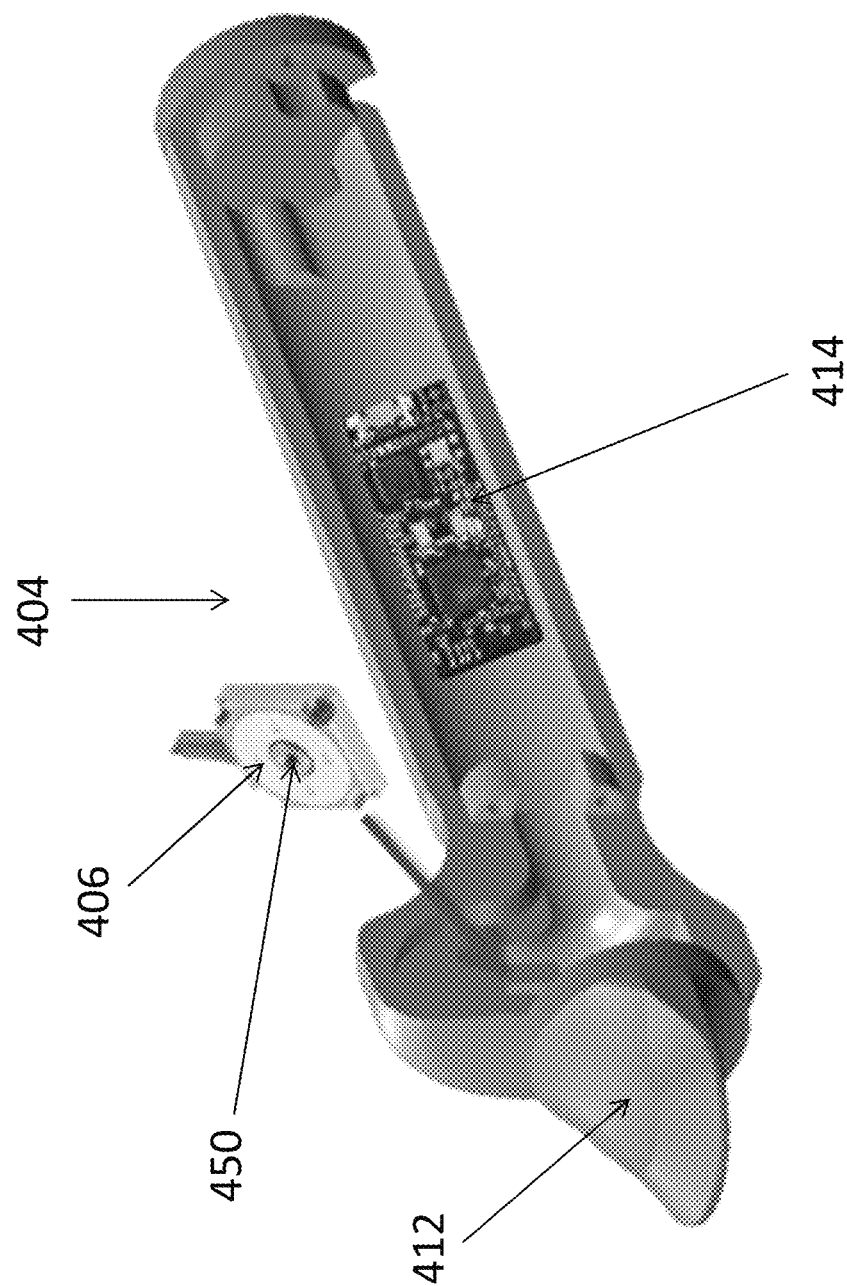
FIG. 27 is a cross-sectional view of the soft tissue device of FIG. 26.

In a further embodiment, an alternative embodiment soft tissue device 404 is disclosed in FIGS. 24 and 25. Soft tissue device 404 includes a force sensor 406, a power supply (not shown), a pressure applicator 410, a handle 412, and an electronics assembly 414 supported within a portion of handle 412. However, handle 412 may be configured with a different shape, as shown in FIGS. 26 and 27 and disclosed as handle 512. As with handles 12, 12', 12", 12''', 12'''', 112, and 212, handles 412, 512 also may be differently configured to accommodate various ergonomic preferences of the therapist, doctor, nurse, clinician, or other professional administrating QSTM to a patient. Soft tissue device 404 of FIGS. 24-29 is configured to operate as previously disclosed herein with respect to soft tissue devices 4, 104, 204.

Figure 28:
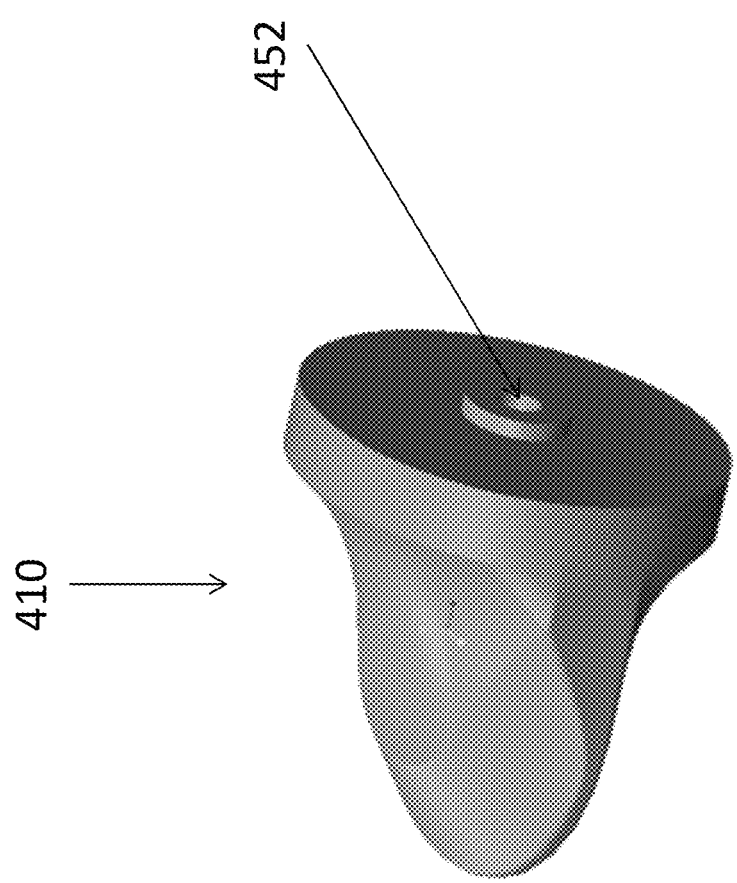
FIG. 28 is a side perspective view of a pressure applicator for a soft tissue device.
Figure 29:
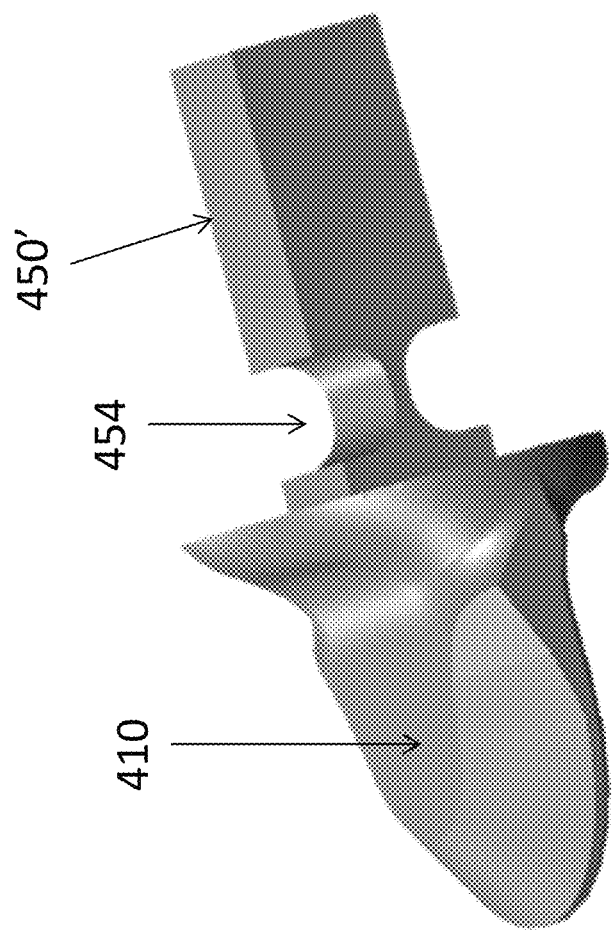
FIG. 29 is a perspective view of the pressure applicator of FIG. 28 coupled with a transmitting shaft.

Illustratively, pressure applicator 410 is electronically coupled to sensor member 406 with a transmitting shaft 450. As shown in FIGS. 28 and 29, transmitting shaft 450 extends from sensor member 406 into an opening 452 at a rear end of pressure applicator 410. Transmitting shaft 450 is configured to measure the force applied to the soft tissue by pressure applicator 410.

Figure 30:
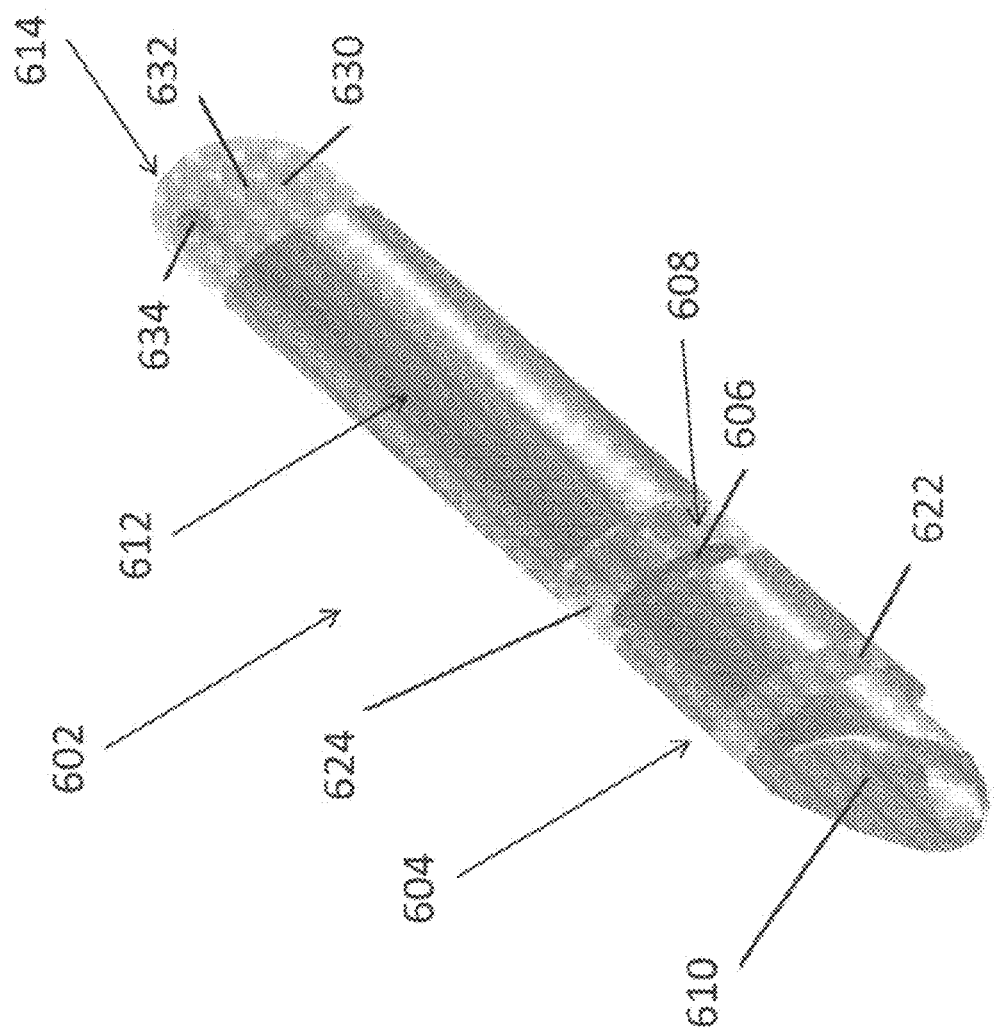
FIG. 30 is a perspective view of a mechanical embodiment soft tissue mobilization system.

Alternatively, as shown in FIG. 30, in a further embodiment, a transmitting shaft 450' extends within a portion of handle 412, 512 and extends between pressure applicator 410 and sensor member 406. Transmitting shaft 450' includes a recessed portion 454 which is configured to receive a portion of sensor member 406 such that, in one embodiment, sensor member 406 extends circumferentially around recessed portion 454.

Figure 31:
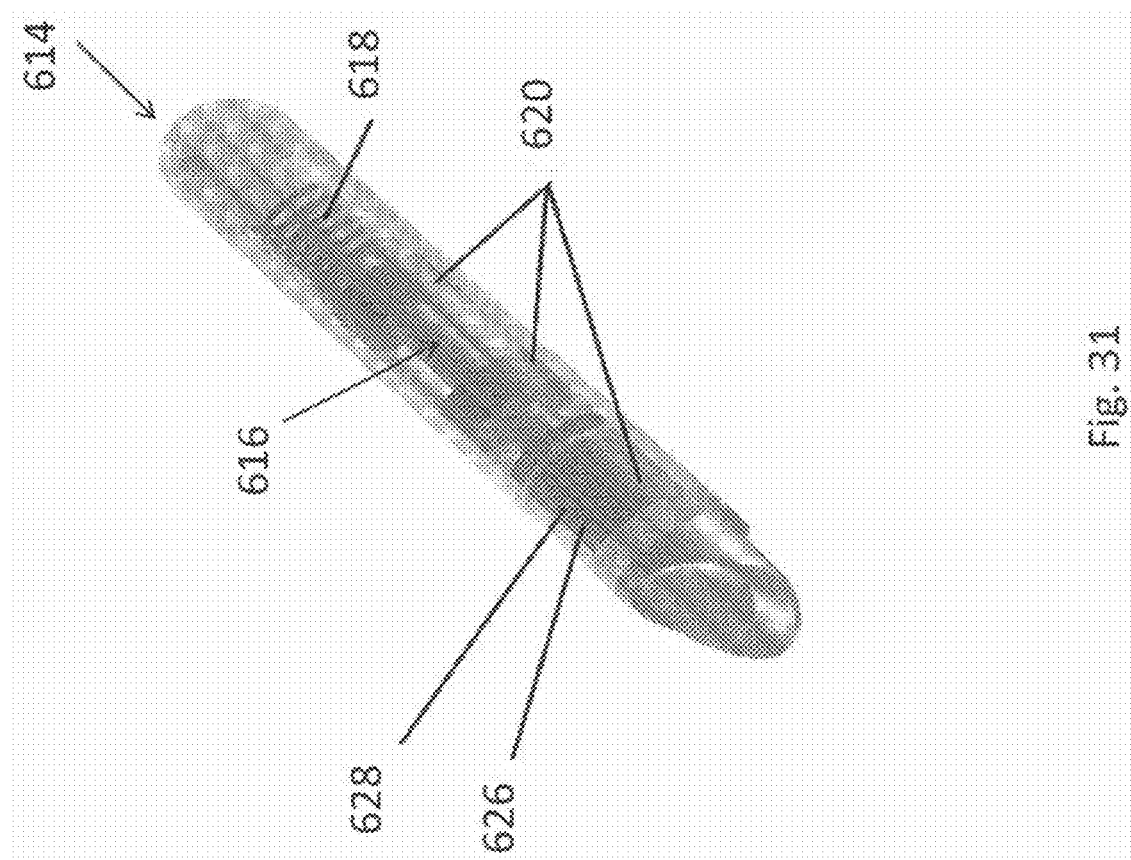
FIG. 31 is a perspective view of the soft tissue mobilization system of FIG. 30 with an outer handle disclosed in phantom.
Figure 32:
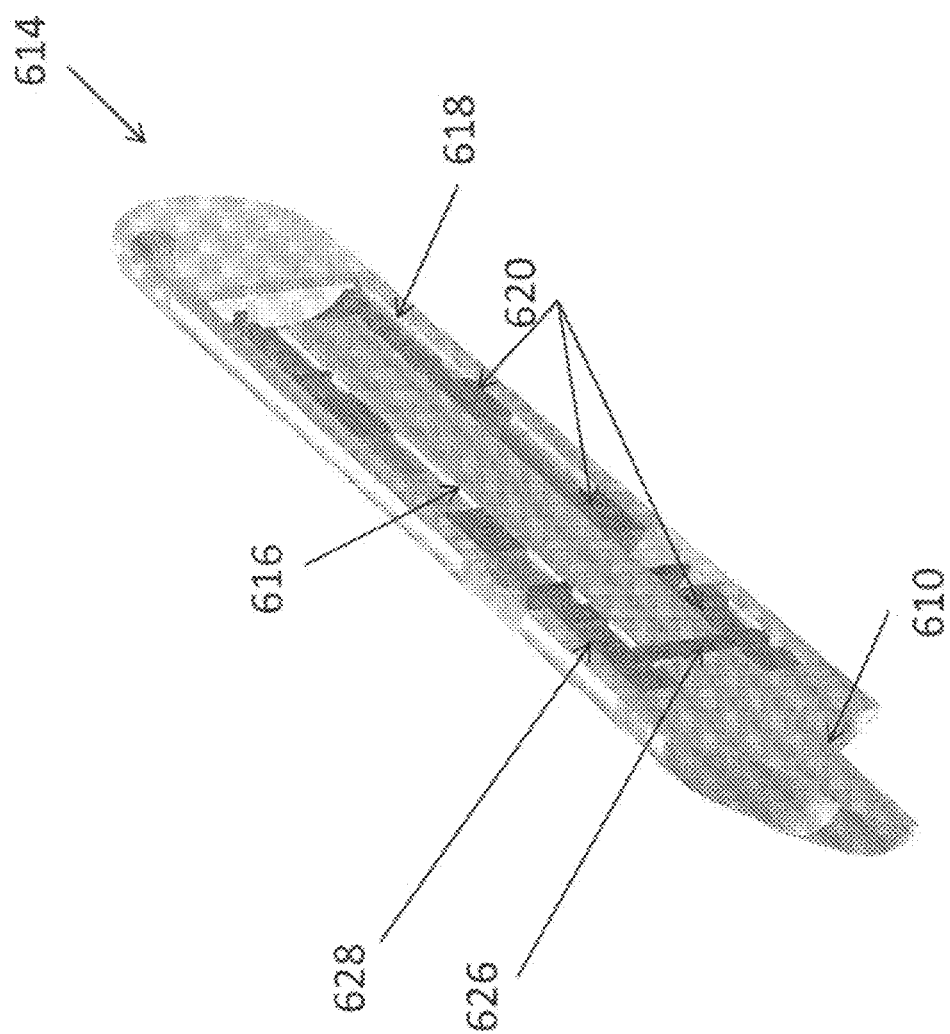
FIG. 32 is a cross-sectional view of the soft tissue mobilization system of FIGS. 30 and 31.

With respect to FIGS. 30-32, a mechanical embodiment of soft tissues mobilization system is disclosed as soft tissue mobilization system 602. Soft tissue mobilization system 602 does not include an electronics assembly and, instead, measures the force applied to the patient's soft tissue using a spring force.

In one embodiment, soft tissue mobilization system 602 includes a soft tissue device 604, a force indicator 606, a visual display 608, a pressure applicator 610, a handle 612, and an orientation indicator 614. Pressure applicator 610 may be similar or identical to any of pressure applicators 10, 110, 210, 410 disclosed herein and is configured to be applied to the soft tissue of a patient and transmit force to the patient's soft tissue during QSTM, as previously disclosed herein. Pressure applicator 610 is mechanically coupled to or integrally formed with a shaft 616 which is operably coupled to a spring 618. Bearings 620 also may be included on shaft 616 to maintain the position of shaft 616 within handle 612. As such, as pressure is applied to the patient's soft tissue, pressure applicator 610 opposes the spring force of spring 618. The movement of spring 618 when pressure applicator 610 acts on spring 618 via shaft 616 is visually indicated to the doctor, clinician, nurse, therapist, or other professional administering QSTM to the patient to provide an indication of the force being applied to the patient's soft tissue.

More particularly, during operation of soft tissue device 604, the doctor, nurse, clinician, therapist, or other professional manually applies pressure to the patient's soft tissue with soft tissue device 604. As the doctor, nurse, clinician, therapist, or other professional applies the force, pressure applicator 610 and shaft 616 may move rearwardly within handle 612 and push against spring 618. Pressure applicator 610 is able to move within handle 612 because a compressible material 622, such as foam, is positioned rearward of pressure applicator 610 and longitudinally intermediate pressure applicator 610 and handle 612. The rearward movement of pressure applicator 610 during QSTM compresses compressible material 622 and the movement of spring 618 is visually displayed to the doctor, nurse, clinician, therapist, or other professional through force indicator 606. Force indicator 606 includes visual indicator 608 which may be a disc or ring fixed to shaft 616 which moves with shaft 616 and is visible to the doctor, nurse, clinician, therapist, or other professional because handle 612 includes a clear or translucent portion or window 624 and visual indicator 608 is shown therein. Window 624 may include numerals, tick marks, or other markings that allow the doctor, nurse, clinician, therapist, or other professional to visually understand and quantify the force applied to the soft tissue.

Soft tissue device 604 further includes a pin 626 positioned within a slot 628 of one of bearings 620. Pin 626 is fixed to shaft 616 and is configured to move with shaft 626 within slot 628. However, pin 626 and slot 628 cooperate to define a hard stop for pressure applicator 610. In other words, pin 626 and slot 628 limit the movement or travel of shaft 616 within handle 612. The length of slot 628 may be configured for a maximum pressure allowed for a QSTM procedure. As such, slot 628 limits the maximum pressure that may be applied to a patient's soft tissue because pin 626 prevents further movement of pressure applicator 610 when in contact with the rear end of slot 628. Alternatively, pin 626 and slot 628 may be eliminated such that the compression of compressible material 622 defines the hard stop and limits the movement of pressure applicator 610 when a maximum force is applied to the patient's soft tissue.

Soft tissue device 604 further includes orientation indicator 614 which, illustratively, includes a clear or translucent end cap 630, a clear or translucent fluid 632 contained within end cap 630, and an indicator 634, illustratively a bubble indicator, configured to move within fluid 632. As the doctor, nurse, clinician, therapist, or other professional aligns soft tissue device 4 with a portion the patient's soft tissue, indicator 634 moves within fluid 632 and the doctor, nurse, clinician, therapist, or other professional can observe and/or record the orientation of indicator 634 to record the alignment of soft tissue device 604 with the patient's soft tissue. In one embodiment, end cap 630 includes tick marks, axes lines, and other markings which allow the doctor, nurse, clinician, therapist, or other professional to evaluate and replicate the position and orientation of soft tissue device 604 with respect to the patient's soft tissue.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains.

What is claimed is:

1. A manually-operated quantification soft tissue mobilization (QSTM) device, comprising:
    a pressure applicator adapted to be moved by a user to dynamically apply a three-dimensional (3D) stroking mechanical force as the pressure applicator is moved by the user in continuous and repeated straight or curved planar gliding motions over a body surface on an area of soft tissue;
    a rigid handle extending from the pressure applicator and adapted to be moved by the user to generate the 3D stroking mechanical force;
    a sensor member coupled to the pressure applicator and including a three-axis force sensor, a three-axis accelerometer and a three-axis gyrometer; and
    an electronic device electronically coupled to the sensor member and configured to provide data integration of outputs from the three-axis force sensor, the three-axis accelerometer and the three-axis gyrometer;
    wherein the sensor member is configured to measure changing magnitudes of the 3D stroking mechanical force being applied, changing angles of the 3D stroking mechanical force being applied, and a plurality of parameters of the 3D stroking mechanical force to provide real-time data feedback to the user as the user is moving the pressure applicator in the continuous and repeated straight or curved planar gliding motions over the body surface on the area of the soft tissue, the plurality of parameters including a stroke duration and a stroke frequency of the 3D stroking mechanical force.

2. The manually-operated QSTM device of claim 1, wherein the rigid handle is configured to be manually grasped by the user.

3. The manually-operated QSTM device of claim 1, wherein the rigid handle includes a first portion and a second portion removably coupled to the first portion.

4. The manually-operated QSTM device of claim 1, wherein the sensor member is positioned intermediate the pressure applicator and the rigid handle.

5. The manually-operated QSTM device of claim 1, wherein the electronic device is configured to receive the outputs from the three-axis force sensor, the three-axis accelerometer and the three-axis gyrometer.

6. The manually-operated QSTM device of claim 1, wherein the electronic device is further configured to determine a position of the pressure applicator relative to the area of soft tissue being treated with the 3D stroking mechanical force.

7. The manually-operated QSTM device of claim 1, wherein the electronic device includes a wireless device.

8. The manually-operated QSTM device of claim 1, wherein a portion of the electronic device is enclosed within the rigid handle.

9. The manually-operated QSTM device of claim 1, wherein the electronic device is configured to determine an orientation angle of the sensor member relative to a skin surface of a patient.

10. The manually-operated QSTM device of claim 1, wherein the sensor member further includes a timer configured to determine the stroke duration.

11. The manually-operated QSTM device of claim 1, wherein the pressure applicator includes a first end configured to contact the soft tissue and a second end spaced apart from the soft tissue, and the sensor member is positioned at the second end of the pressure applicator.

12. The manually-operated QSTM device of claim 1, wherein the pressure applicator includes a first end having a continuous flat surface configured to contact the soft tissue and a second end spaced apart from the soft tissue.

13. The manually-operated QSTM device of claim 1, wherein the pressure applicator is integrally formed with the rigid handle such that the pressure applicator is immovable relative to the QSTM device and configured to contact the area of soft tissue.

14. The manually-operated QSTM device of claim 1, wherein a sole stimulus applied to the soft tissue by the pressure applicator is the 3D stroking mechanical force by the user.

15. The manually-operated QSTM device of claim 1, wherein the pressure applicator is not coupled to a solenoid, an electric motor, or a pneumatic transducer, and does not provide an electrical, ultrasound, or vibration stimulation.

16. The manually-operated QSTM device of claim 1, further comprising a power supply.

17. The manually-operated QSTM device of claim 1, further comprising a display member electronically coupled to the electronic device to provide the real-time data feedback to the user regarding the 3D stroking mechanical force.

18. The manually-operated QSTM device of claim 17, wherein the display member is electronically coupled to the sensor member through at least one of a wired connection or a wireless connection.

19. The manually-operated QSTM device of claim 17, further comprising a computing device having a memory and operably coupled to the display member.

20. The manually-operated QSTM device of claim 19, wherein at least one of the electronic device or the computing device is configured to store data from the sensor member associated with the 3D stroking mechanical force.

21. The manually-operated QSTM device of claim 17, wherein the display member includes one or more of a visual output and an audio output.

22. The manually-operated QSTM device of claim 1, wherein the pressure applicator is made of one or more materials comprising a stainless steel, a carbon-based material, and a polymeric resin.

23. The manually-operated QSTM device of claim 1, wherein the sensor member is operably coupled to the pressure applicator through a pressure transmitter.

24. A method of quantifying an applied force to soft tissue, comprising:
applying, with a pressure applicator of a quantification soft tissue mobilization (QSTM) device, a three-dimensional (3D) stroking mechanical force by a user in continuous and repeated straight or curved planar gliding motions over a body surface on an area of soft tissue;
measuring, with a sensor member of the QSTM device that includes a three-axis force sensor, a three-axis accelerometer and a three-axis gyrometer, changing magnitudes of the 3D stroking mechanical force being applied, changing angles of the 3D stroking mechanical force being applied, and a plurality of parameters of the 3D stroking mechanical force to provide real-time data feedback to the user as the user is moving the pressure applicator in the continuous and repeated straight or curved planar gliding motions over the body surface on the area of the soft tissue, the plurality of parameters including a stroke duration and a stroke frequency of the 3D stroking mechanical force;
receiving, by an electronic assembly of the QSTM device, outputs from the three-axis force sensor, the three-axis accelerometer and the three-axis gyrometer comprising the sensor member;
providing, by the electronic assembly of the QSTM device, data integration of the outputs of the three-axis force sensor, the three-axis accelerometer and the three-axis gyrometer; and transmitting, by the electronic assembly of the QSTM device, the outputs to be visually displayed.

25. The method of claim 24, further comprising:
determining, by the electronic assembly of the QSTM device, an orientation angle of the sensor member relative to a skin surface of a patient.

26. The method of claim 24, wherein the pressure applicator includes a first end and a second end, and the method further comprises:
contacting the soft tissue with the first end of the pressure applicator; and
spacing apart the second end from the soft tissue.

27. The method of claim 26, further comprising positioning the sensor member at the second end of the pressure applicator.

28. The method of claim 24, further comprising:
providing an audio readout of the outputs from the three-axis force sensor, the three-axis accelerometer and the three-axis gyrometer.

29. The method of claim 24, further comprising:
providing a display member to visually display the outputs from the three-axis force sensor, the three-axis accelerometer and the three-axis gyrometer.

30. The method of claim 24, wherein transmitting the outputs includes wirelessly transmitting the outputs.

31. The method of claim 30, wherein wirelessly transmitting the outputs includes using a wireless signal to transmit the outputs.

32. The method of claim 24, further comprising:
storing, by the electronic assembly of the QSTM device, the outputs from the three-axis force sensor, the three-axis accelerometer and the three-axis gyrometer.

33. A manually-operated quantification soft tissue mobilization (QSTM) device, comprising:
a pressure applicator integrally formed with a rigid handle such that the pressure applicator is immovable relative to the QSTM device and configured to contact an area of soft tissue of a patient and is adapted to be moved by a user to dynamically apply a three-dimensional (3D) stroking mechanical force to the contacted area of soft tissue as the pressure applicator is moved by the user in continuous and repeated straight or curved planar gliding motions over the contacted area of soft tissue, wherein a sole stimulus applied to the contacted area of soft tissue by the pressure applicator is the 3D stroking mechanical force and the 3D stroking mechanical force results from user generated movements of the rigid handle;
the rigid handle extending from the pressure applicator and including a first portion and a second portion removably coupled to the first portion;
a sensor member including a three-axis force sensor, a three-axis accelerometer, a three-axis gyrometer and a timer, the sensor member configured to measure changing magnitudes of the 3D stroking mechanical force being applied, changing angles of the 3D stroking mechanical force being applied, and a plurality of parameters of the 3D stroking mechanical force in real-time as the pressure applicator is moved by the user in the continuous and repeated straight or curved planar gliding motions over the contacted area of the soft tissue, the plurality of parameters including a stroke duration and a stroke frequency of the 3D stroking mechanical force;
an electronic device electronically coupled to the sensor member and configured to provide data integration of outputs from the three-axis force sensor, the three-axis accelerometer and the three-axis gyrometer;
a power supply;
a visual display electronically coupled to the electronic device that provides real-time data feedback to the user regarding the 3D stroking mechanical force on the contacted area of soft tissue; and
a computing device having a memory and operably coupled to the visual display;
wherein the electronic device and/or the computing device is configured to record and store data measured by the sensor member associated with the 3D stroking mechanical force.

34. The manually-operated QSTM device of claim 33, wherein the electronic device is configured to receive the outputs from the three-axis force sensor, the three-axis accelerometer and the three-axis gyrometer.

35. The manually-operated QSTM device of claim 34, wherein the electronic device is further configured to provide an audio readout of the outputs from the three-axis force sensor, the three-axis accelerometer and the three-axis gyrometer.

36. The manually-operated QSTM device of claim 33, wherein the pressure applicator does not provide an electrical, ultrasound, or vibration stimulation to the contacted area of the soft tissue of the patient.

37. The manually-operated QSTM device of claim 33, wherein the pressure applicator is not coupled to a solenoid, an electric motor, or a pneumatic transducer.

38. The manually-operated QSTM device of claim 33, wherein the electronic device includes a wireless device.

39. The manually-operated QSTM device of claim 33, wherein:
the pressure applicator includes a first end that contacts the soft tissue and a second end spaced apart from the soft tissue; and
the sensor member is positioned at the second end of the pressure applicator.

40. The manually-operated QSTM device of claim 33, wherein the visual display is electronically coupled to the sensor member through at least one of a wired connection or a wireless connection.

41. The manually-operated QSTM device of claim 33, wherein the visual display includes a visual output and/or an audio output.

42. The manually-operated QSTM device of claim 33, wherein the pressure applicator is a material comprising stainless steel, a carbon-based material, and/or a polymeric resin.

43. The manually-operated QSTM device of claim 33, wherein the sensor member is operably coupled to the pressure applicator through a pressure transmitter.

44. A method of treating an area of soft tissue of a patient, comprising:
providing a dynamically applied three-dimensional (3D) stroking mechanical force by a handheld device as a sole stimulus to the area of soft tissue, the handheld device including a sensor member, a rigid handle and a pressure applicator, the pressure applicator being integrally formed with the rigid handle and immovable relative to the handheld device by contacting the area of soft tissue with the pressure applicator, the 3D stroking mechanical force resulting from movements of the rigid handle by a user of the handheld device in continuous and repeated straight or curved planar gliding motions over the area of soft tissue;
measuring changing magnitudes of the 3D stroking mechanical force being applied, changing angles of the 3D stroking mechanical force being applied, and a plurality of parameters of the 3D stroking mechanical force by the sensor member, the sensor member including a three-axis force sensor, a three-axis accelerometer and a three-axis gyrometer, the plurality of parameters including a stroke duration and a stroke frequency of the 3D stroking mechanical force;
receiving outputs of the three-axis force sensor, the three-axis accelerometer and the three-axis gyrometer; providing data integration of the outputs of the three-axis force sensor, the three-axis accelerometer and the three-axis gyrometer;
determining one or more treatment parameters related to the area of soft tissue being treated with the 3D stroking mechanical force;
visually displaying real-time data feedback to the user regarding the one or more treatment parameters related to the area of soft tissue being treated with the 3D stroking mechanical force;
monitoring the real-time data feedback;
adjusting the 3D stroking mechanical force provided to the area of soft tissue based upon the real-time data feedback; and
storing the real-time data feedback regarding the one or more treatment parameters related to the area of soft tissue being treated with the 3D stroking mechanical force.

45. The method of claim 44, wherein adjusting the 3D stroking mechanical force provided to the area of soft tissue is further based upon another dataset selected from a group consisting of stored data from a previous treatment of the patient, and data related to a type of pressure that is most effective for a particular injury or disease.

46. The method of claim 44, wherein the area of soft tissue being treated with the 3D stroking mechanical force is a location of an injury or a disease.

47. The method of claim 44, wherein visually displaying the real-time data feedback to the user includes displaying the real-time data feedback on a display member.

48. The method of claim 47, wherein the display member is an LED or LCD monitor, display, or screen.

* * * * *